(12) United States Patent
Feshin et al.

(10) Patent No.: US 11,584,777 B2
(45) Date of Patent: Feb. 21, 2023

(54) METHOD FOR PURIFYING A SULFATASE PROTEIN

(71) Applicant: GREEN CROSS CORPORATION, Yongin-si (KR)

(72) Inventors: Denis Feshin, Yongin-si (KR); Byung Hyun Park, Yongin-si (KR); Yong Won Shin, Yongin-si (KR)

(73) Assignee: GREEN CROSS CORPORATION, Yongin (KR)

( * ) Notice: Subject to any disclaimer, the term of this patent is extended or adjusted under 35 U.S.C. 154(b) by 449 days.

(21) Appl. No.: 16/643,355

(22) PCT Filed: Aug. 31, 2017

(86) PCT No.: PCT/KR2017/009561
§ 371 (c)(1),
(2) Date: Feb. 28, 2020

(87) PCT Pub. No.: WO2019/045149
PCT Pub. Date: Mar. 7, 2019

(65) Prior Publication Data
US 2020/0361985 A1 Nov. 19, 2020

(51) Int. Cl.
| C07K 1/22 | (2006.01) |
| C07K 1/18 | (2006.01) |
| C07K 1/36 | (2006.01) |
| C12N 9/16 | (2006.01) |
| C07K 1/34 | (2006.01) |

(52) U.S. Cl.
CPC .............. *C07K 1/22* (2013.01); *C07K 1/18* (2013.01); *C07K 1/36* (2013.01); *C12N 9/16* (2013.01); *C07K 1/34* (2013.01); *C12Y 301/06* (2013.01)

(58) Field of Classification Search
None
See application file for complete search history.

(56) References Cited

U.S. PATENT DOCUMENTS

| 2004/0161837 A1 | 8/2004 | Reuser et al. |
| 2012/0189605 A1* | 7/2012 | Koppaka ............. A61P 25/02 424/94.6 |
| 2013/0330802 A1 | 12/2013 | Mihara et al. |
| 2016/0083454 A1 | 3/2016 | Duthe et al. |

FOREIGN PATENT DOCUMENTS

| EP | 2532742 A1 | 12/2012 |
| JP | 2002-510486 A | 4/2002 |
| JP | 2004-208684 A | 7/2004 |
| JP | 2006-510356 A | 3/2006 |
| JP | 2009-273469 A | 11/2009 |
| JP | 2010-515434 A | 5/2010 |
| JP | 2011-509674 A | 3/2011 |
| JP | 2011-525523 A | 9/2011 |
| JP | 2013-532986 A | 8/2013 |
| JP | 2016-504040 A | 2/2016 |
| JP | 2016-519137 A | 6/2016 |
| JP | 2016-196506 A | 11/2016 |
| KR | 10-2016-0005047 A | 1/2016 |
| KR | 10-1598897 B1 | 3/2016 |
| WO | 2009/156430 A1 | 12/2009 |
| WO | 2012/159053 A1 | 11/2012 |

OTHER PUBLICATIONS

Helwig et al., "Purification and Some Properties of Arylsulphatases A and B from Rabbit Kidney Cortex", Biochem J. 165: 127-134 (Year: 1977).*
Yadilette Rivera-Colon, et al., "The structure of human GALNS reveals the molecular basis for mucopolysaccharidosis IV A", Journal of Molecular Biology, Aug. 29, 2012 (online), pp. 1-27, vol. 423, No. 5.
International Search Report for PCT/KR2017/009561 dated May 15, 2018 (PCT/ISA/210).
Written Opinion for PCT/KR2017/009561 dated May 15, 2018 (PCT/ISA/237).

* cited by examiner

*Primary Examiner* — Anand U Desai
(74) *Attorney, Agent, or Firm* — Sughrue Mion, PLLC

(57) ABSTRACT

A method for purification of a sulfatase using metal chelating chromatography without using tags such as His-tag, etc. is disclosed. An embodiment provides a method for purifying a sulfatase including the steps of: (a) providing a sulfatase-containing solution comprising one or a plurality of impurities; (b) performing a first chromatographic separation of the sulfatase-containing solution using a metal affinity chromatography resin; (c) performing a second chromatographic separation using a cation exchange chromatography resin; and (d) performing a final chromatographic separation using an anion exchange chromatography resin, wherein the impurities are removed thereby.

14 Claims, 15 Drawing Sheets
Specification includes a Sequence Listing.

[Figure 1]
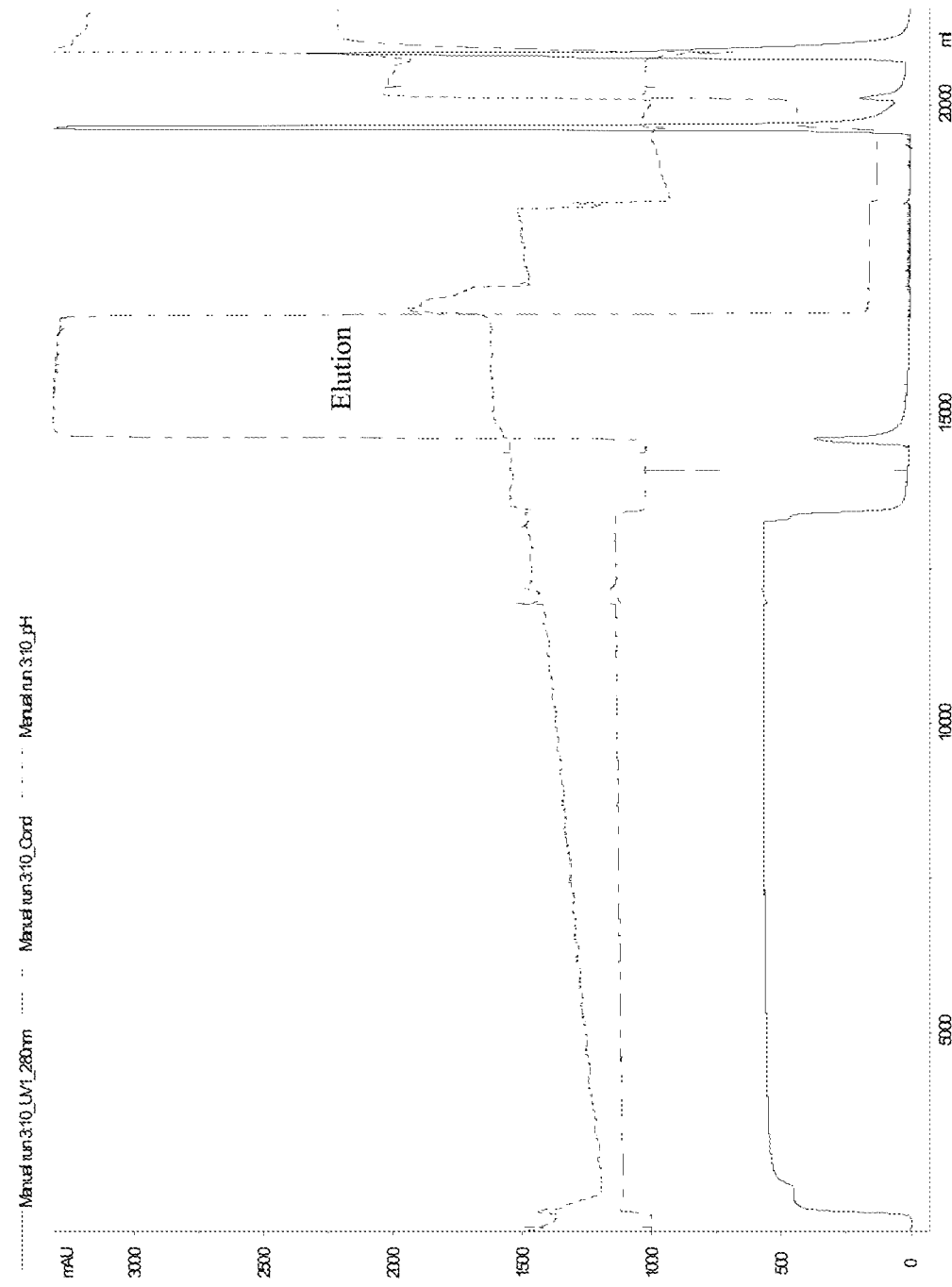

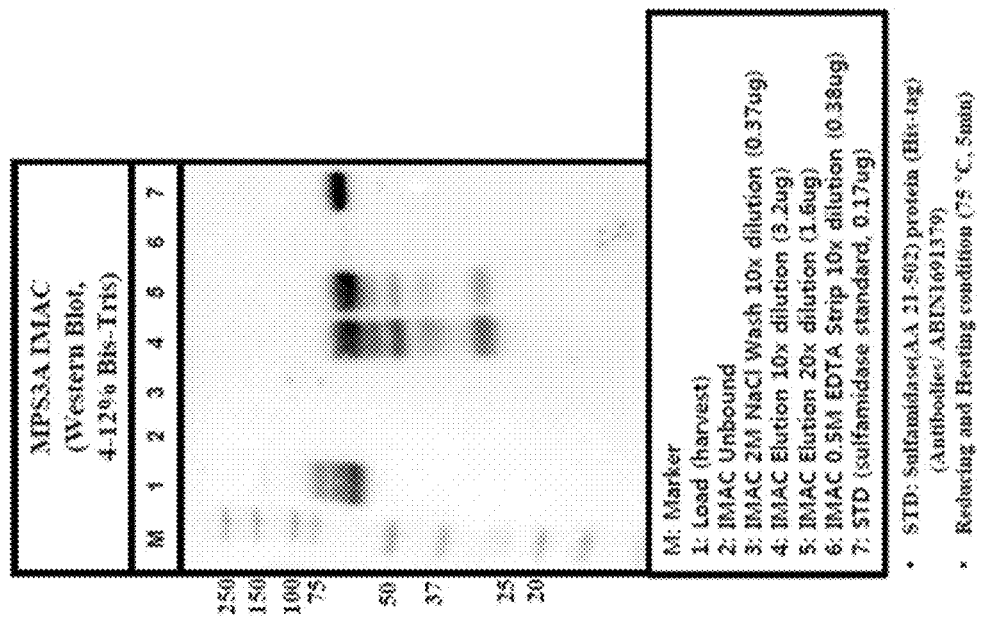
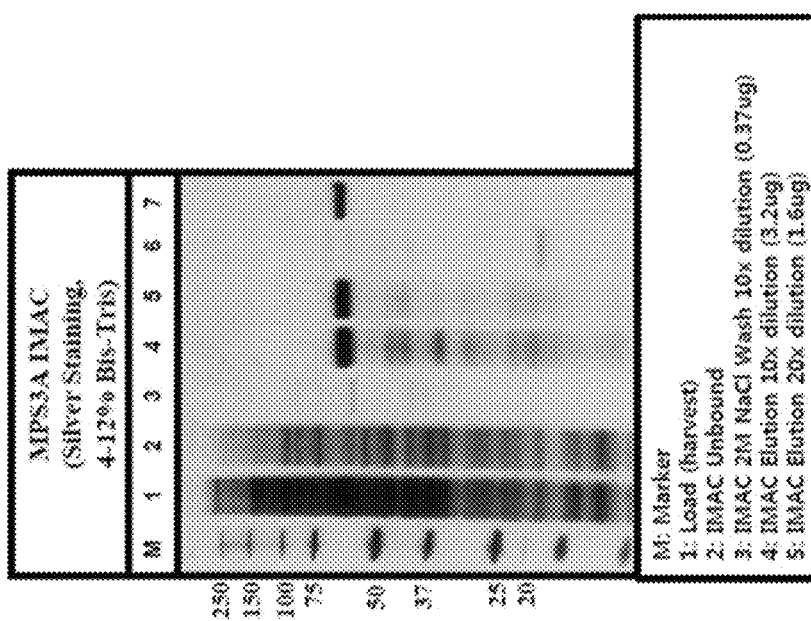
[Figure 2]

[Figure 3]
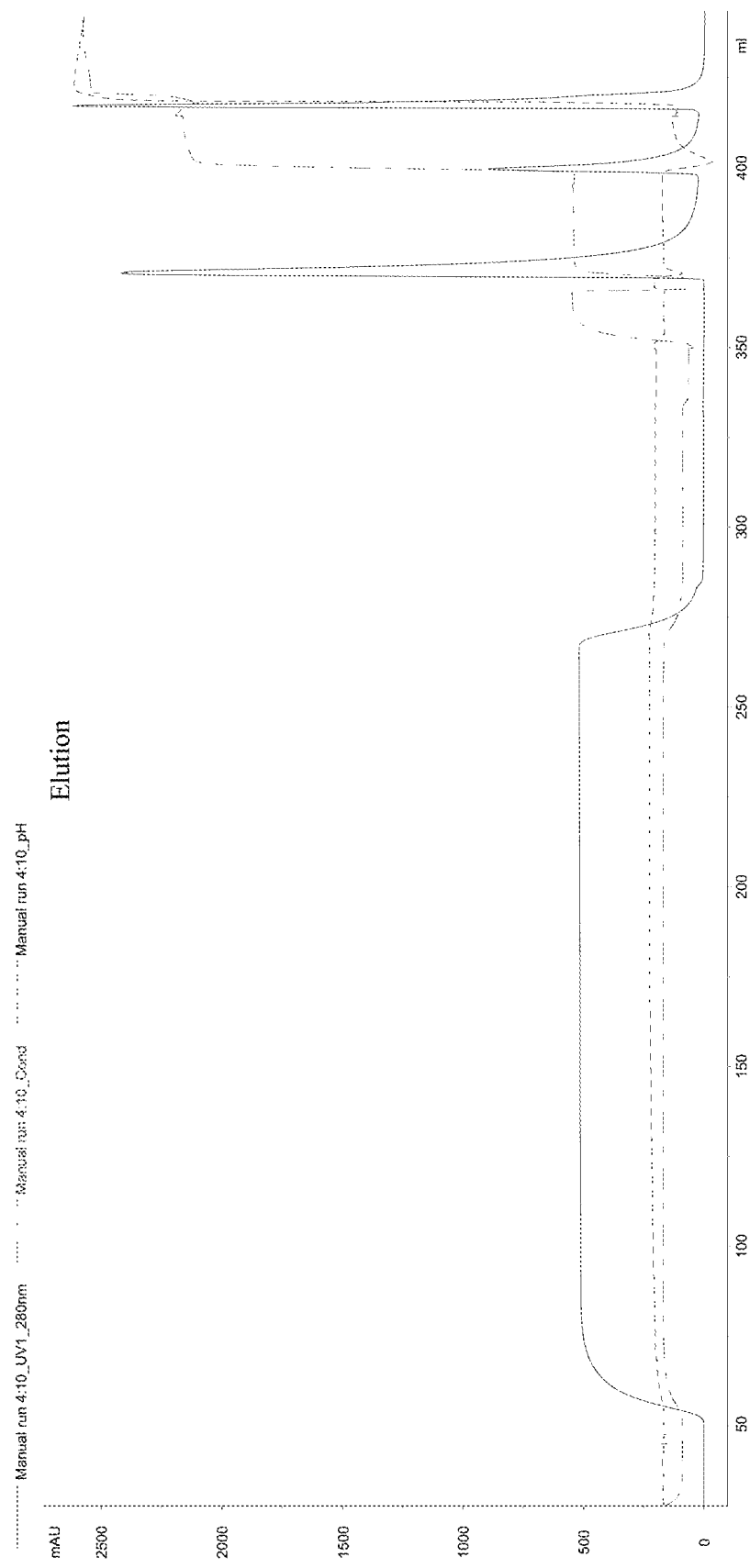

[Figure 4]
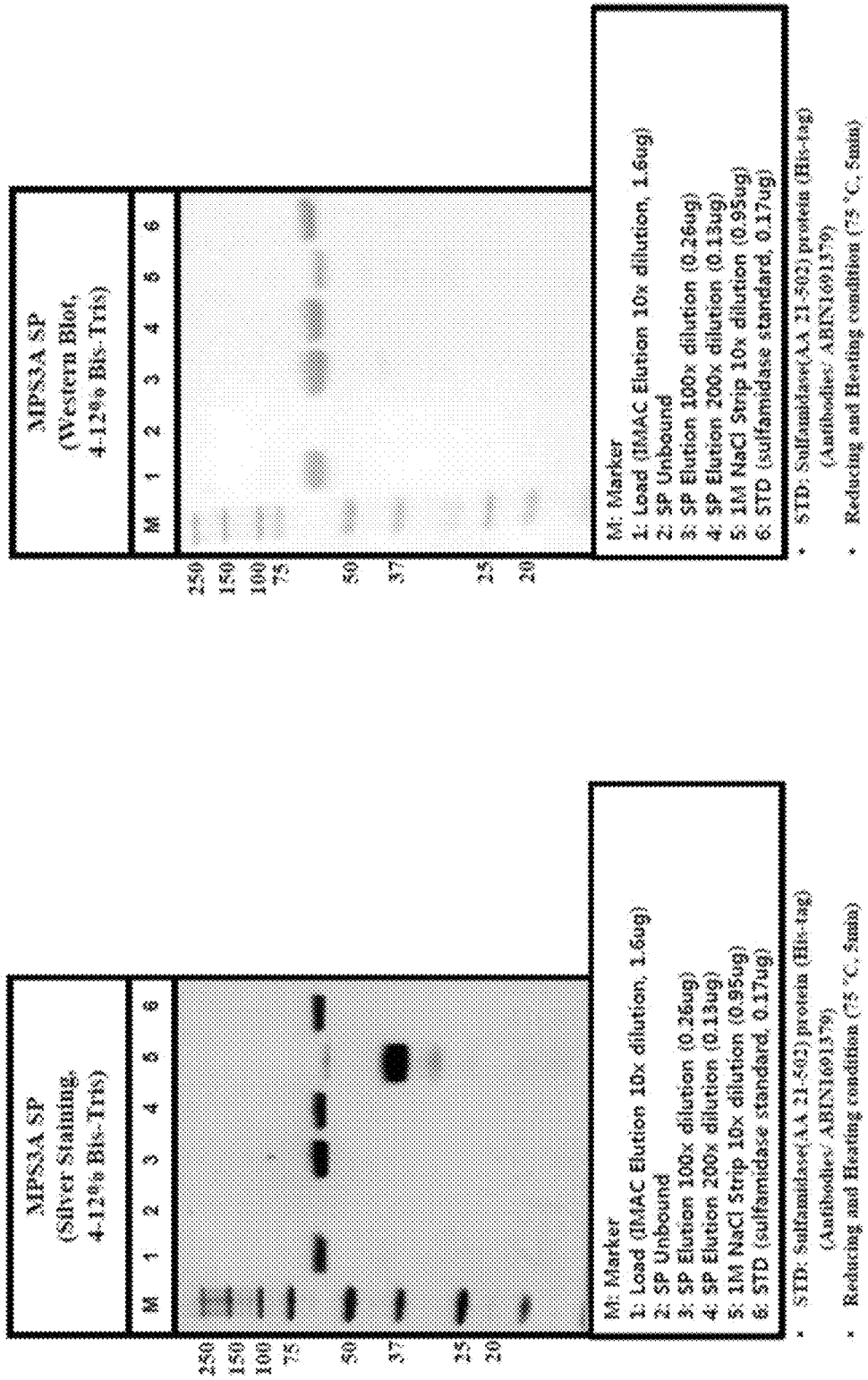

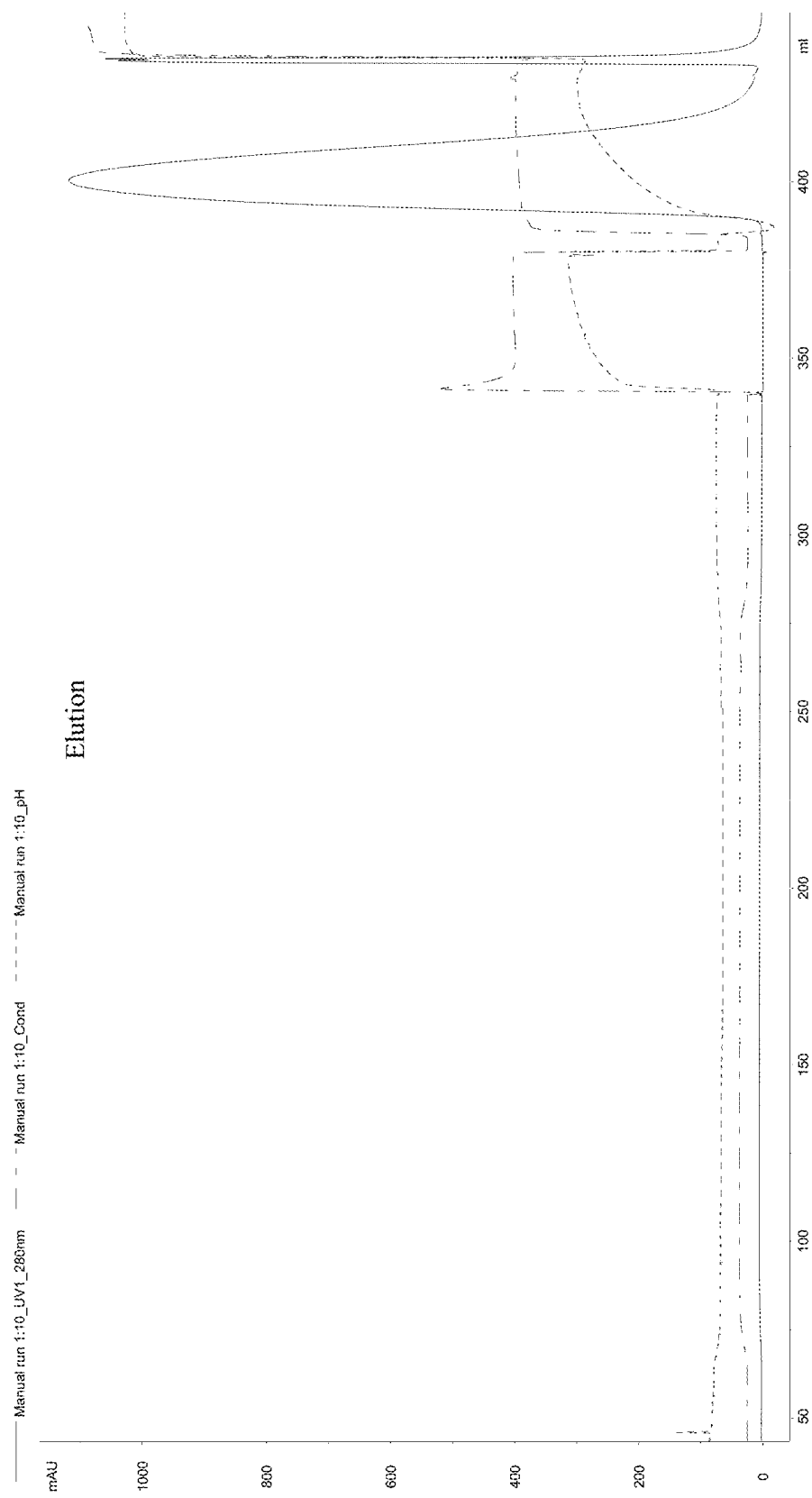
[Figure 5]

[Figure 6]
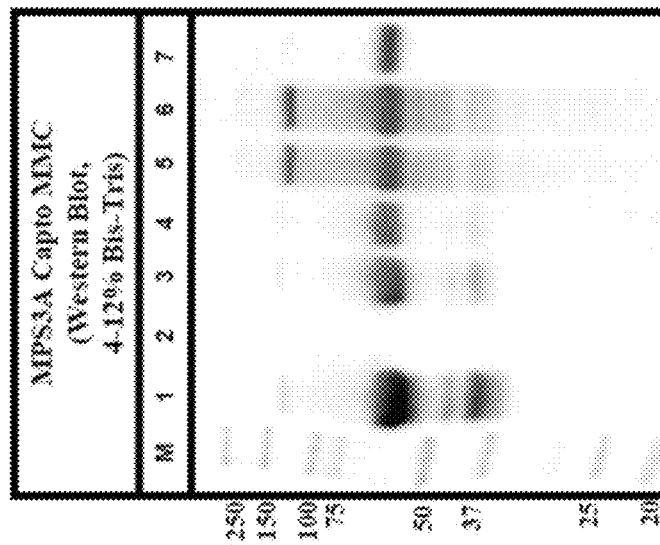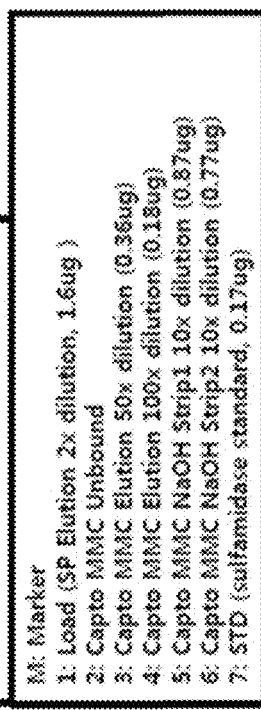
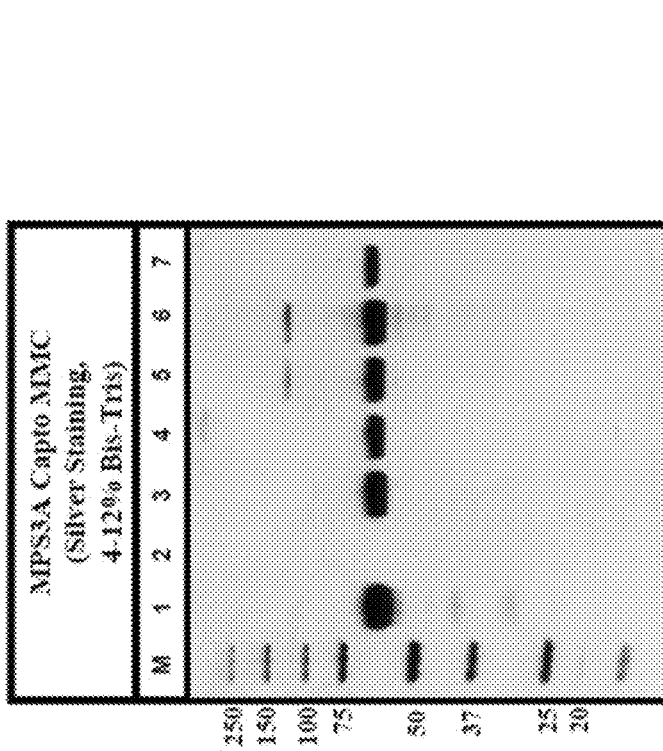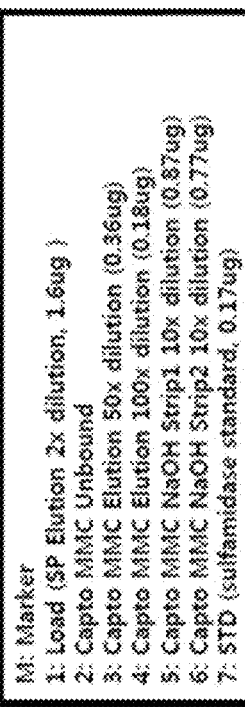

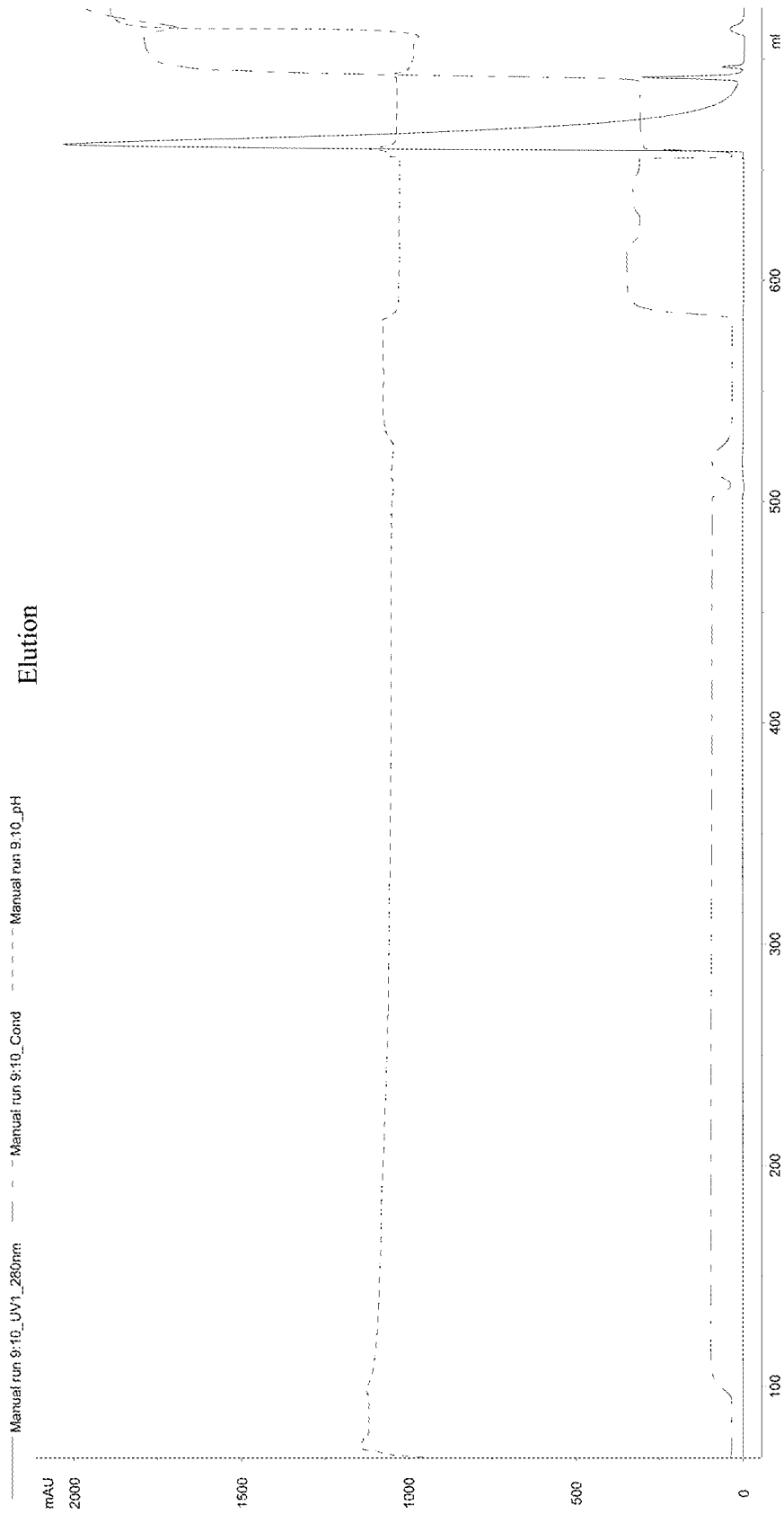
[Figure 7]

[Figure 8]
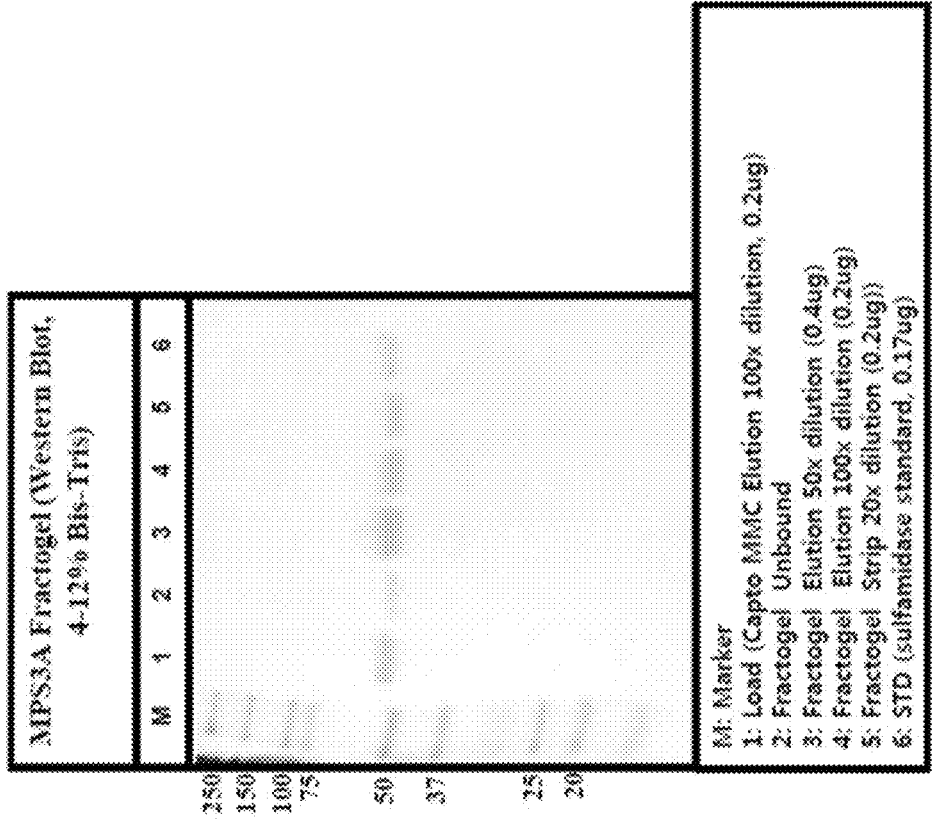
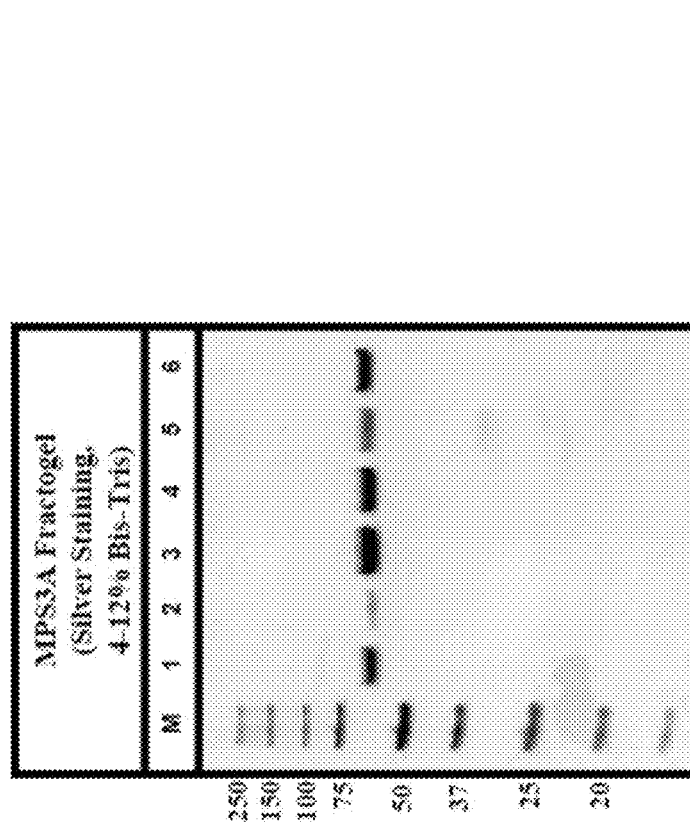

[Figure 9]
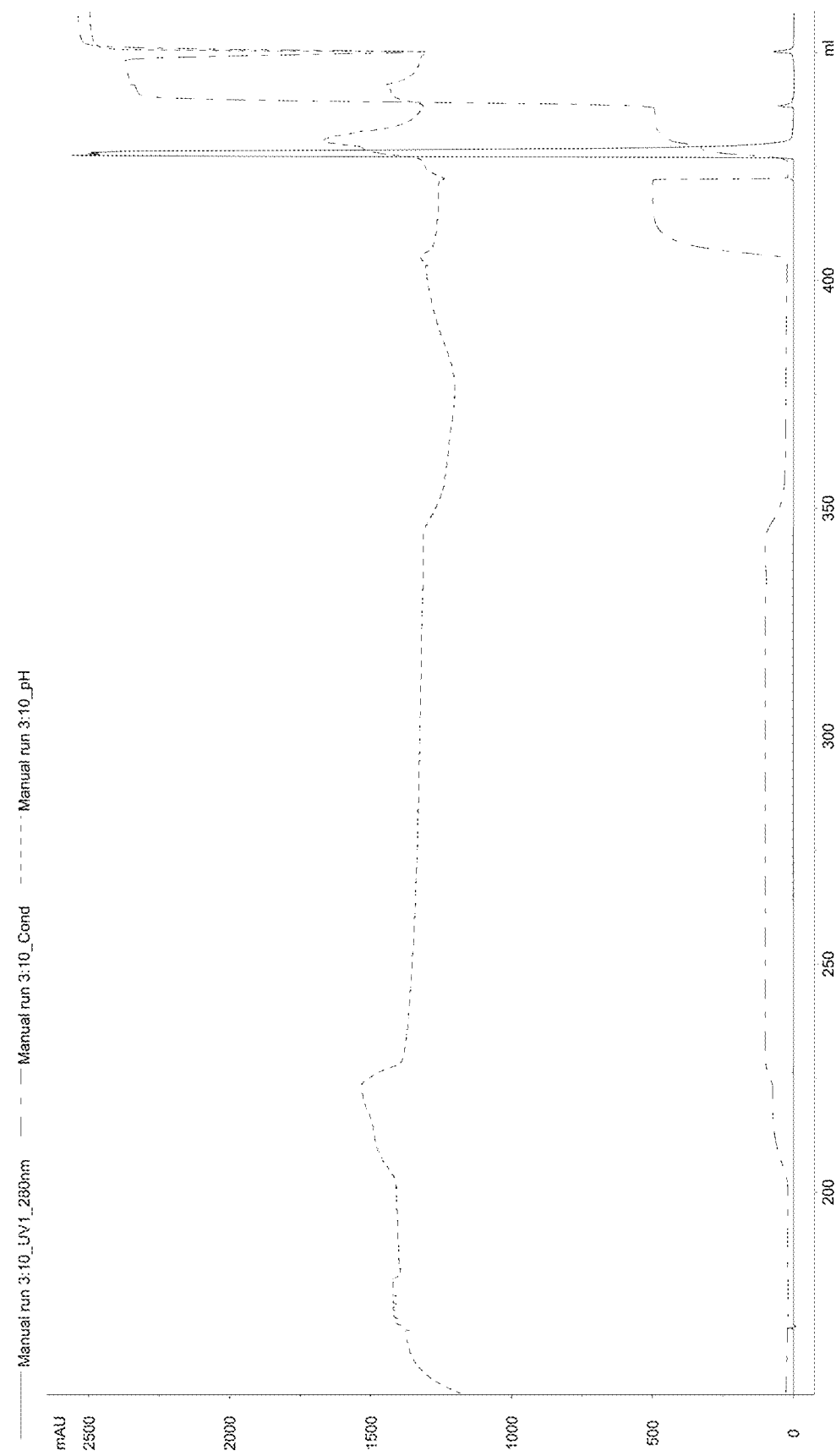

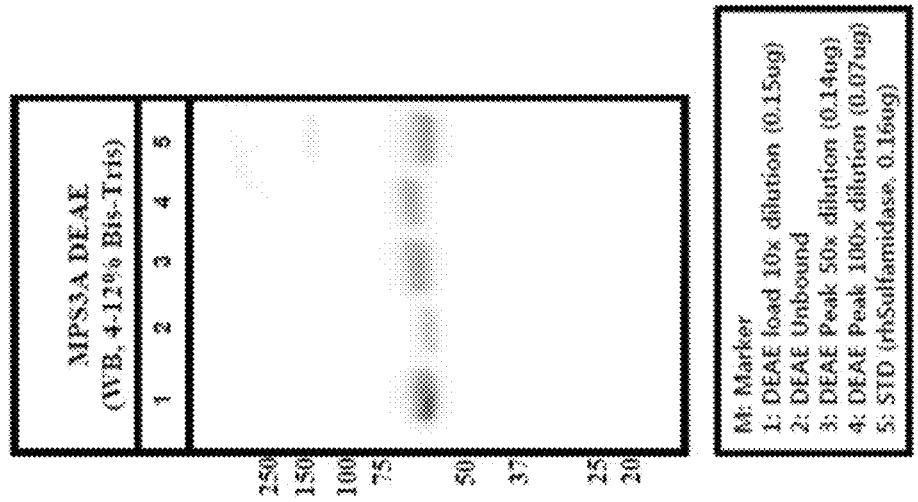
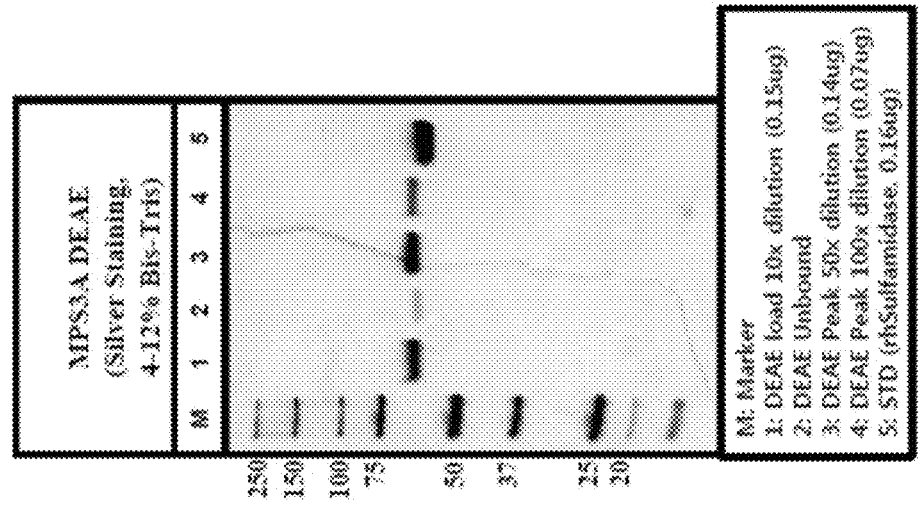
[Figure 10]

[Figure 11]
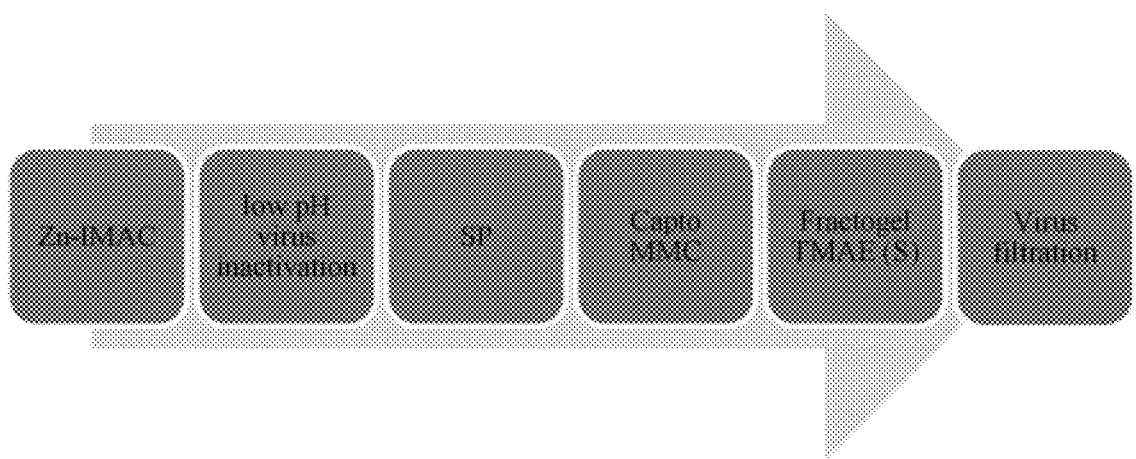

[Figure 12]
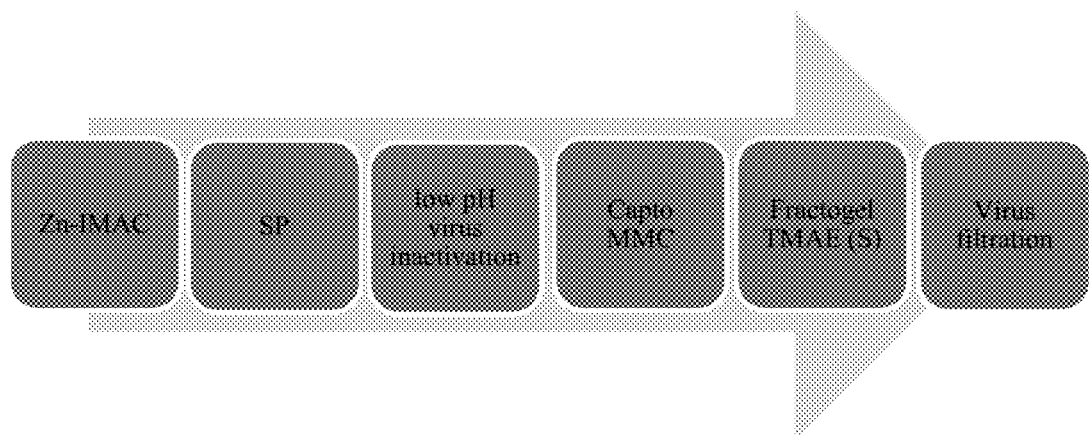

[Figure 13]
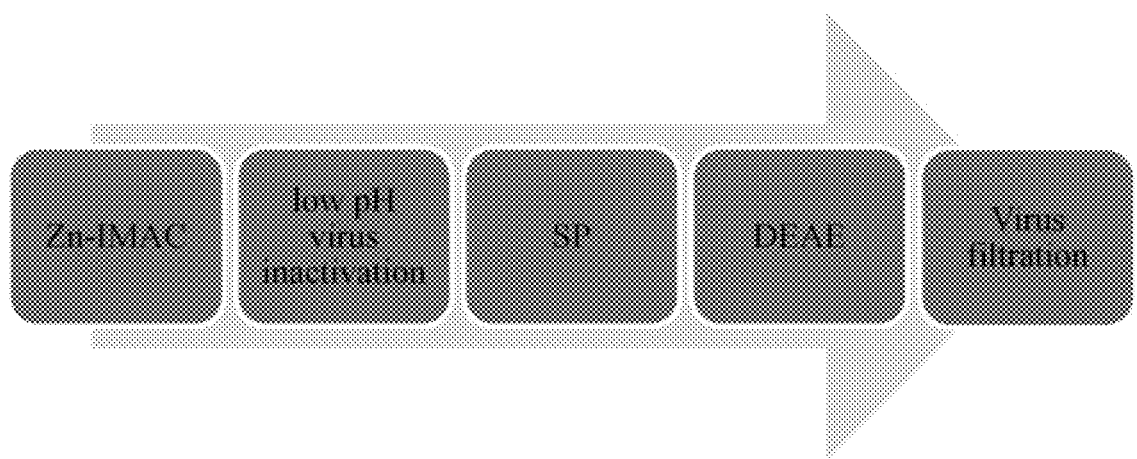

[Figure 14]
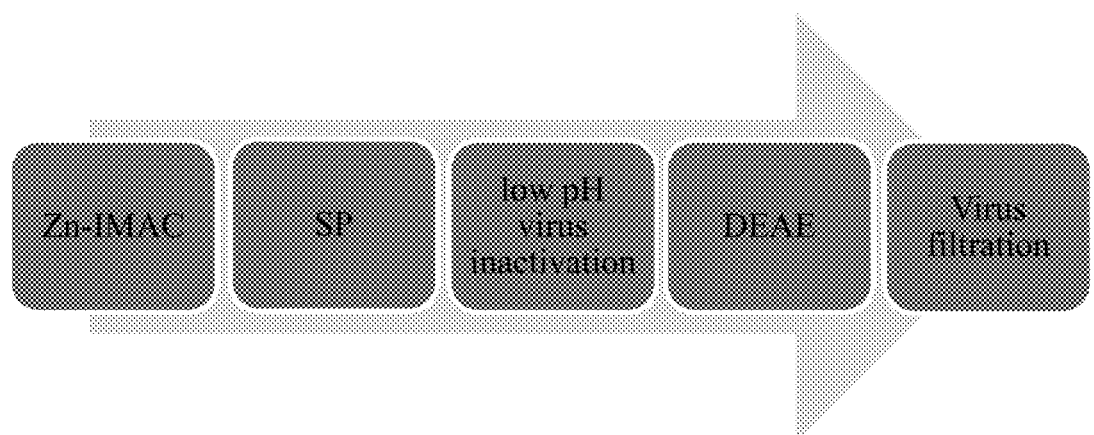

[Figure 15]
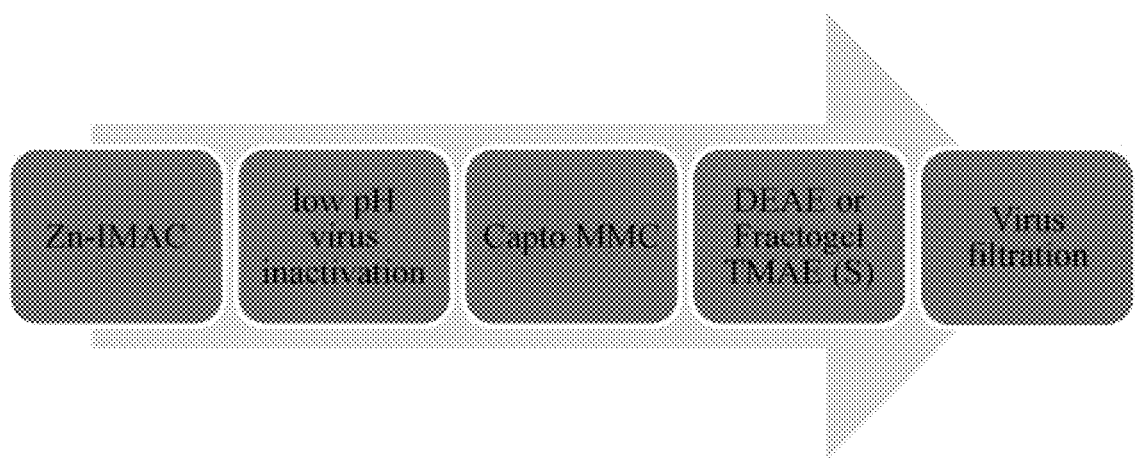

SEQUENCE LISTING

<160> NUMBER OF SEQ ID NOS: 1

<210> SEQ ID NO 1

```
<211> LENGTH: 502
<212> TYPE: PRT
<213> ORGANISM: Homo sapiens

<400> SEQUENCE: 1

Met Ser Cys Pro Val Pro Ala Cys Cys Ala Leu Leu Leu Val Leu Gly
1               5                   10                  15

Leu Cys Arg Ala Arg Pro Arg Asn Ala Leu Leu Leu Ala Asp Asp
            20                  25                  30

Gly Gly Phe Glu Ser Gly Ala Tyr Asn Asn Ser Ala Ile Ala Thr Pro
            35                  40                  45

His Leu Asp Ala Leu Ala Arg Arg Ser Leu Leu Phe Arg Asn Ala Phe
    50                  55                  60

Thr Ser Val Ser Ser Cys Ser Pro Ser Arg Ala Ser Leu Leu Thr Gly
65                  70                  75                  80

Leu Pro Gln His Gln Asn Gly Met Tyr Gly Leu His Gln Asp Val His
                85                  90                  95

His Phe Asn Ser Phe Asp Lys Val Arg Ser Leu Pro Leu Leu Leu Ser
            100                 105                 110

Gln Ala Gly Val Arg Thr Gly Ile Ile Gly Lys Lys His Val Gly Pro
        115                 120                 125

Glu Thr Val Tyr Pro Phe Asp Phe Ala Tyr Thr Glu Glu Asn Gly Ser
    130                 135                 140

Val Leu Gln Val Gly Arg Asn Ile Thr Arg Ile Lys Leu Leu Val Arg
145                 150                 155                 160

Lys Phe Leu Gln Thr Gln Asp Arg Pro Phe Phe Leu Tyr Val Ala
                165                 170                 175

Phe His Asp Pro His Arg Cys Gly His Ser Gln Pro Gln Tyr Gly Thr
            180                 185                 190

Phe Cys Glu Lys Phe Gly Asn Gly Glu Ser Gly Met Gly Arg Ile Pro
        195                 200                 205

Asp Trp Thr Pro Gln Ala Tyr Asp Pro Leu Asp Val Leu Val Pro Tyr
    210                 215                 220

Phe Val Pro Asn Thr Pro Ala Ala Arg Ala Asp Leu Ala Ala Gln Tyr
225                 230                 235                 240

Thr Thr Val Gly Arg Met Asp Gln Gly Val Gly Leu Val Leu Gln Glu
                245                 250                 255

Leu Arg Asp Ala Gly Val Leu Asn Asp Thr Leu Val Ile Phe Thr Ser
            260                 265                 270

Asp Asn Gly Ile Pro Phe Pro Ser Gly Arg Thr Asn Leu Tyr Trp Pro
        275                 280                 285

Gly Thr Ala Glu Pro Leu Leu Val Ser Ser Pro Glu His Pro Lys Arg
    290                 295                 300

Trp Gly Gln Val Ser Glu Ala Tyr Val Ser Leu Leu Asp Leu Thr Pro
305                 310                 315                 320

Thr Ile Leu Asp Trp Phe Ser Ile Pro Tyr Pro Ser Tyr Ala Ile Phe
                325                 330                 335

Gly Ser Lys Thr Ile His Leu Thr Gly Arg Ser Leu Leu Pro Ala Leu
            340                 345                 350

Glu Ala Glu Pro Leu Trp Ala Thr Val Phe Gly Ser Gln Ser His His
        355                 360                 365

Glu Val Thr Met Ser Tyr Pro Met Arg Ser Val Gln His Arg His Phe
    370                 375                 380

Arg Leu Val His Asn Leu Asn Phe Lys Met Pro Phe Pro Ile Asp Gln
```

-continued

```
            385                 390                 395                 400
Asp Phe Tyr Val Ser Pro Thr Phe Gln Asp Leu Leu Asn Arg Thr Thr
                    405                 410                 415

Ala Gly Gln Pro Thr Gly Trp Tyr Lys Asp Leu Arg His Tyr Tyr Tyr
                420                 425                 430

Arg Ala Arg Trp Glu Leu Tyr Asp Arg Ser Arg Asp Pro His Glu Thr
            435                 440                 445

Gln Asn Leu Ala Thr Asp Pro Arg Phe Ala Gln Leu Leu Glu Met Leu
        450                 455                 460

Arg Asp Gln Leu Ala Lys Trp Gln Trp Glu Thr His Asp Pro Trp Val
465                 470                 475                 480

Cys Ala Pro Asp Gly Val Leu Glu Glu Lys Leu Ser Pro Gln Cys Gln
                485                 490                 495

Pro Leu His Asn Glu Leu
                500
```

METHOD FOR PURIFYING A SULFATASE PROTEIN

CROSS REFERENCE TO RELATED APPLICATIONS

This application is a National Stage of International Application No. PCT/KR2017/009561 filed Aug. 31, 2017.

TECHNICAL FIELD

This invention is related to a new method for purifying a sulfatase protein.

BACKGROUND ART

The mucopolysaccharidoses (MPS) are a group of rare, inherited lysosomal storage disorders caused by the deficiency or absence of specific lysosomal enzymes. The absence of these enzymes results in the accumulation of complex sugar molecules in the cells and tissues, as well as in cellular organelles called lysosomes. In the presence of normal lysosomal enzymes these sugars are transformed into other substances and used by the body. These complex sugars are known as mucopolysaccharides or glycosaminoglycans (GAGs) and serve as the building blocks for connective tissues in the body.

MPS III results from the lack of four different enzymes necessary to degrade the GAG. Each enzyme deficiency defines a different form of Sanfilippo syndrome: type IIIA (Sanfilippo A), type IIIB (Sanfilippo B), type IIIC (Sanfilippo C), and type IIID (Sanfilippo D).

Heparan-N-sulfatase (HNS) is an enzyme that participates in the stepwise degradation of heparan sulfate. HNS hydrolyzes the sulfate moiety attached to the amino group of the glucosamine residue of heparan sulfate, a type of GAG. A deficiency of this enzyme is associated with mucopolysaccharidoses IIIA (MPS, Sanfilippo's syndrome A). Patients affected by MPS type III A have mutations in the gene coding for HNS, resulting in a dis-function, deficiency or absence of this enzyme.

Symptoms of MPS IIIA (Sanfilippo A) usually arise between 2 to 6 years of age, although in some cases diagnosis is made as late as 13 years of age. The clinical symptoms of the condition present with differing degrees of severity. The central nervous system is the most severely affected system in patients with MPS IIIA. HNS and other secondarily stored compounds accumulate primarily in the central nervous system. Problems in language development, motor skills, and intellectual development characterize the condition. Overall, individuals with MPS IIIA have a marked developmental delay, and long-term survival is poor. The condition is chronically debilitating and life-threatening.

Presently no approved therapeutic treatments for MPS IIIA are available. Bone marrow transplant has been used in an attempt to slow disease progression. Because heparan sulfate is the natural substrate of HNS, animal studies have shown that HNS may be useful for the treatment of lysosomal storage disorders, such as MPS IIIA, in which there is an increase in heparan sulfate.

Immobilized metal affinity chromatography (IMAC), also known as metal chelate affinity chromatography (MCAC), is a specialized aspect of affinity chromatography. The principle behind IMAC lies in the fact that many transition metal ions, i.e., zinc, copper, nikel, cobalt and others, can coordinate to the amino acids histidine, cysteine, and tryptophan via electron donor groups on the amino acid side chains. To utilize this interaction for chromatographic purposes, the metal ion must be immobilized onto an insoluble support. This can be done by attaching a chelating group to the chromatographic matrix.

The most common chelating group used in this technique is iminodiacetic acid (IDA). It is coupled to a matrix such as SEPHAROSE 6B, via a long hydrophilic spacer arm. The spacer arm ensures that the chelating metal is fully accessible to all available binding sites on a protein. Another popular chelating group for IMAC applications is tris-(carboxymethyl)-ethylenediamine (TED). This particular group lends different properties to the gel than IDA. TED gels show stronger retention of metal ions and weaker retention of proteins relative to that of IDA gels. TED gels form a complex (single coordination site) vs a chelate (multiple coordination sites for IDA gels. Nitrilo triacetic acid (NTA) is a tetradentate ligand which attempts to balance the metal anchoring strength with metal-ion protein interaction properties (Hochuli, E., H. Dobeli, A. Schacher [1987] J. Chromatography 411:177-184). Other chelating ligands have been reported and are mentioned. See, e.g., Porath (1992), supra. The most commonly used metals for IMAC are zinc and copper; however, nickel cobalt, and calcium have also been used successfully and should be tested at development step.

The development of IMAC in purification processes can be vacillated considerably by accurate prediction of the protein affinity of a given protein for IMAC resins before performing separations in the laboratory. If the affinity for an IMAC resin could be reliably and easily predicted from its protein structure, then the researcher would be better informed when deciding on a development strategy. A protein predicted to have a high affinity, for example could be bound to a resin under relatively stringent conditions and eluted with a simple isocratic step. In contrast, IMAC should not be considered as a primary purification step for a protein predicted to possess a low affinity to the metal-chelating resins.

Zn-Chelating Chromatography has been utilized in the clinical production of human interleukin-4 (h IL-4), human interleukin-10 (h IL-10) and human tissue plasminogen activator (h tPA). IMAC relies primarily on the interaction between Histidine (His) and a metal ion reversibly bound to a stationery phase. Although immobilized, Zn is extensively used because its selectivity, other metal ions like $Cu^{2+}$, $Ni^{2+}$, and $Co^{2+}$ are also applied for certain proteins. Interactions between immobilized metals and tryptophan, tyrosine, or cysteine residues of proteins have been reported, however, these are generally weaker interactions. Furthermore, when a histidine lies in close proximity to an aromatic residue or another histidine (e.g. on the same position of successive turns of an alpha helix), a cooperative effect leading to high affinity is observed. Although protein leader sequences containing His-Tyr, His-Trp, His-X-X-His, have been engineered to take advantage of this phenomenon, these sequences are relatively rare in nature. With naturally occurring proteins, therefore, one can generalize that affinity of a protein for conventional IMAC resins is dictated by the availability of His side chain, imidazole.

DISCLOSURE

Technical Problem

Given the interest in HNS as a pharmaceutical agent, there remains a need for preparation of large quantities of highly purified material in a cost effective manner. Various reports of purifying HNS from culture medium have been reported (Hemsley et al., Mol. Genet. Metab. 90:313-328 (2007)).

While several methods of purification of HNS have been attempted and described, those methods include multiple steps of buffer exchange by ultra-filtration/dia-filtration (UF/DF), followed by filtration of precipitated proteins (for example, for harvest), to fit load pH and conductivity to ion-exchange chromatography conditions. These steps normally lead to a protein loss on the surface of the membranes of the filters, as well as increase duration and operational and capital expenses of the purification.

It has not been previously reported if Heparan-N-sulfatase can be purified using metal chelating chromatography without use of tags (such as His-tag, etc.).

This invention provides simple and effective methods for purification of Heparan-N-sulfatase (HNS), which is suitable for efficient production of such proteins for use in human therapy.

Technical Solution

1. A method for purifying a sulfatase comprising the steps of: (a) providing a sulfatase-containing solution comprising one or a plurality of impurities; (b) performing a first chromatographic separation of the sulfatase-containing solution using a metal affinity chromatography resin; (c) performing a second chromatographic separation using a cation exchange chromatography resin; and (d) performing a final chromatographic separation using an anion exchange chromatography resin, wherein the impurities are removed thereby.

2. The method of said technical solution 1, wherein the metal affinity chromatography resin is charged with a divalent metal cation.

3. The method of said technical solution 2, wherein the divalent metal is zinc.

4. The method of claim 1, wherein the cation exchange chromatography resin is selected from the group consisting of a strong cation exchange chromatography resin and a multimodal cation exchange chromatography resin.

5. The method of said technical solution 1, further comprising the step of performing a third chromatographic separation using a cation exchange chromatography resin, wherein the resin used in the second chromatographic separation step is a strong cation exchange chromatography resin; and wherein the resin used in the third chromatographic separation step is a multimodal cation exchange chromatography resin.

6. The method of said technical solution 1, wherein the anion exchange chromatography resin is selected from the group consisting of a strong anion exchange chromatography resin and a weak anion exchange chromatography resin.

7. The method of said technical solution 1, wherein the sulfatase has a metal ion selected from the group consisting of a calcium ion, a ferrous ion, a ferric ion, and a zinc ion in its active site.

8. The method of said technical solution 1, wherein the sulfatase is selected from the group consisting of heparan-N-sulfatase, arylsulfatase A (ASA, or human lysosomal cerebroside-3-sulfate 3-sulfohydrolase), arylsulfatase B (ASB, or human lysosomal N-acetylgalactosamine-4-sulfate 4-sulfohydrolase), human oestrone/dehydroepiandrosterone sulfatase, human lysosomal (N-acetyl)galactosamine-6-sulfatase (GALNS), arylsulfatase from *P. aeruginosa*, and sulfatase/hydrolase from B. caryophylli PG2952 (BcPMH).

9. The method of said technical solution 1, further comprising a step of low pH virus inactivation 10. The method of said technical solution 9, wherein the low pH virus inactivation step is performed after the first chromatographic separation step and before the second chromatographic separation step; or after the second chromatographic separation step and before the final chromatographic separation step.

11. The method of said technical solution 5, further comprising a step of low pH virus inactivation.

12. The method of said technical solution 11, wherein the low pH virus inactivation step is performed after the first chromatographic separation step and before the second chromatographic separation step; or after the second chromatographic separation step and before the third chromatographic separation step.

13. The method of said technical solution 1, further comprising a step of virus filtration.

14. The method of said technical solution 13, wherein the virus filtration step is performed after the final chromatographic separation step.

15. The method of said technical solution 1, wherein the sulfatase-containing solution is selected from the group consisting of a cell culture harvest and partially purified intermediate solutions.

Advantageous Effects

The method according to an embodiment is advantageous in that harvest can be loaded to a sorbent without any specific treatment such as dilution, buffer exchange or pH/conductivity adjustment by ultra-filtration/dia-filtration (UF/DF).

The method according to an embodiment is advantageous in that elution can be performed by pH change or/and eluting agents.

The method according to an embodiment allows reducing expenses for membrane filters and related equipment (i.e. filter holders, peristaltic pumps), reducing the volume of buffers, shortening time required for purification.

The method according to an embodiment is advantageous in that virus inactivation by solvent/detergent treatment (S/D) can be performed before the chromatography by adding required chemicals to a harvest. Detergents, such as Triton X100 which is often used for virus inactivation, don't affect binding of the protein to a sorbent.

The method according to an embodiment is advantageous in that virus inactivation by low pH can be performed after elution of the protein of interest from the sorbent. In case of metal chelating chromatography, low pH elution allows minimizing time spend required for preparation for this step (normally UF/DF and filtration if precipitation occurs).

The method according to an embodiment is advantageous in that it simplifies purification process with significant reduction of the timing and amount of materials needed. Additionally, required virus inactivation steps can be implemented easily when purifying therapeutic protein(s).

DESCRIPTION OF DRAWINGS

FIG. 1 shows a chromatogram of Zn-IMAC purification of HNS protein.

FIG. 2 shows a silver staining gel and a western blot gel of Zn-IMAC purification of HNS protein.

FIG. 3 shows a chromatogram of SP-sepharose purification of HNS protein.

FIG. 4 shows a silver staining gel and a western blot gel of SP purification of HNS protein.

FIG. 5 shows a chromatogram of Capto MMC purification of HNS protein.

FIG. 6 shows a silver staining gel and a western blot gel of Capto MMC purification of HNS protein.

FIG. 7 shows a chromatogram of Fractogel TMAE (S) purification of HNS protein.

FIG. 8 shows a silver staining gel and a western blot gel of Fractogel TMAE (S) purification of HNS protein.

FIG. 9 shows a chromatogram of DEAE purification of HNS protein.

FIG. 10 shows a silver staining gel and a western blot gel of DEAE purification of HNS protein.

FIG. 11 shows the flow chart of a purification method according to the example 1.

FIG. 12 shows the flow chart of a purification method according to the example 1 with low pH virus inactivation after SP chromatography.

FIG. 13 shows the flow chart of a purification method according to the example 2.

FIG. 14 shows the flow chart of a purification method according to the example 2 with low pH virus inactivation after SP chromatography.

FIG. 15 shows the flow chart of a purification method according to the example 3.

BEST MODE

As described in detail below, the present inventors have successfully developed a method for purification of a sulfatase, including but not limited to Heparan-N-sulfatase, using metal chelating chromatography without use of tags (such as His-tag, etc.).

An embodiment provides a method for purifying a sulfatase comprising the steps of: (a) providing a sulfatase-containing solution comprising one or a plurality of impurities; (b) performing a first chromatographic separation of the sulfatase-containing solution using a metal affinity chromatography resin; (c) performing a second chromatographic separation using a cation exchange chromatography resin; and (d) performing a final chromatographic separation using an anion exchange chromatography resin, wherein the impurities are removed thereby.

In an embodiment, the metal affinity chromatography resin is charged with a divalent metal cation. In an embodiment, the divalent metal is zinc. In an embodiment, the cation exchange chromatography resin is selected from the group consisting of a strong cation exchange chromatography resin and a multimodal cation exchange chromatography resin. In an embodiment, the strong cation exchange chromatography resin is SP sepharose. In an embodiment, the multimodal cation exchange chromatography resin is Capto MMC.

In an embodiment, the method for purifying a sulfatase further comprises the step of performing a third chromatographic separation using a cation exchange chromatography resin, wherein the resin used in the second chromatographic separation step is a strong cation exchange chromatography resin; and wherein the resin used in the third chromatographic separation step is a multimodal cation exchange chromatography resin. In an embodiment, the strong cation exchange chromatography resin is SP sepharose. In an embodiment, the multimodal cation exchange chromatography resin is Capto MMC.

In an embodiment, the anion exchange chromatography resin of the first chromatographic separation step is selected from the group consisting of a strong anion exchange chromatography resin and a weak anion exchange chromatography resin. In an embodiment, the strong anion exchange chromatography resin is Fractogel TMAE (S). In an embodiment, the weak anion exchange chromatography resin is DEAE.

In an embodiment, the sulfatase being purified has a calcium ion in its active site. In an embodiment, the sulfatase being purified is selected from the group consisting of heparan-N-sulfatase, arylsulfatase A (ASA, or human lysosomal cerebroside-3-sulfate 3-sulfohydrolase), arylsulfatase B (ASB, or human lysosomal N-acetylgalactosamine-4-sulfate 4-sulfohydrolase), human oestrone/dehydroepiandrosterone sulfatase, human lysosomal (N-acetyl)galactosamine-6-sulfatase (GALNS), arylsulfatase from *P. aeruginosa*, and sulfatase/hydrolase from B. caryophylli PG2952 (BcPMH).

In an embodiment, the sulfatase being purified has a sequence identical to SEQ ID NO: 1. In an embodiment, the sulfatase being purified has a sequence at least 99%, 98%, 97%, 96%, 95%, 94%, 93%, 92%, 91%, 90%, 89%, 88%, 87%, 86%, 85%, 84%, 83%, 82%, 81%, 80%, 79%, 78%, 77%, 76%, 75%, 74%, 73%, 72%, 71%, 70%, 69%, 68%, 67%, 66%, 65%, 64%, 63%, 62%, 61%, 60%, 59%, 58%, 57%, 56%, 55%, 54%, 53%, 52%, 51%, 50%, 49%, 48%, 47%, 46%, 45%, 44%, 43%, 42%, 41% or 40% similar to SEQ ID NO: 1.

In an embodiment, the method for purifying a sulfatase further comprises a step of low pH virus inactivation. In an embodiment, wherein the first, the second and the final chromatographic separation steps are performed, the low pH virus inactivation step is performed after the first chromatographic separation step and before the second chromatographic separation step; or after the second chromatographic separation step and before the final chromatographic separation step. In an embodiment, wherein the first, the second, the third and the final chromatographic separation steps are performed, the low pH virus inactivation step is performed after the first chromatographic separation step and before the second chromatographic separation step; after the second chromatographic separation step and before the third chromatographic separation step; or after the third chromatographic separation step and before the final chromatographic separation step.

In an embodiment, the method for purifying a sulfatase further comprises the step of virus filtration. In an embodiment, the virus filtration step is performed after the final chromatographic separation step.

In an embodiment, the sulfatase-containing solution is any form of solution that contains a sulfatase. In an embodiment, the sulfatase-containing solution is a cell culture harvest. In an embodiment, the sulfatase-containing solution is a partially purified intermediate solution. In an embodiment, the partially purified intermediate solution is a solution obtained from any previous chromatographic separation or any previous buffer exchange by UF/DF.

An embodiment described herein provides methods and processes for preparing purified HNS, a lysosomal enzyme for use in the treatment of MPS IIIA. An embodiments described herein provides methods of treating a subject (e.g., a subject with MPS IIIA) with the purified HNS compositions disclosed herein. Processes for purifying HNS are known in the art. See e.g., Hemsley et al., Mol. Genet. Metab. 90:313-328 (2007); U.S. Patent Application Pub. No. 2009/0186011 each of which is incorporated herein by reference.

Producing and purifying HNS according to methods disclosed herein provides HNS that contains reduced amounts of contaminants. The HNS produced by methods described herein is particularly well suited for use as a therapeutic agent (e.g., for the treatment of MPS IIIA).

Heparan-N-sulfatase (SEQ ID NO: 1) is a lysosomal enzyme also known in the art by the names N-sulphoglucosamine sulphohydrolase; SGSH; EC 3.10.1.1; N-sulfoglucosamine sulfohydrolase; 2-desoxy-D-glucoside-2-sulphamate sulphohydrolase (sulphamate sulphohydrolase); heparin sulfamidase; sulfoglucosamine sulfamidase; sulphamidase; HNS, rhHNS, sulfamidase, rhNS, and rhSGSH. The term "HNS" as used herein encompasses this enzyme, including functional fragments and/or derivatives thereof, and any pharmaceutically acceptable forms thereof Heparan-N-sulfase is associated with Online Mendelian Inheritance in Man (OMIM) identification no. OMIM 605270, the entry for which is publicly available online at www.ncbi.nlm.nih.gov/omim/605270. The entire contents of this online entry, and all pages linked thereon, are herein incorporated by reference.

As used herein, "HNS composition" means any composition containing HNS, in various states of purity.

As used herein, the term "substantially pure" means that the proteins or polypeptides are essentially free of other substances to an extent practical and appropriate for their intended use. In particular, the proteins are sufficiently pure and are sufficiently free from other biological constituents of their hosts cells and viruses so as to be useful in, for example, pharmaceutical preparations. As used herein, a "substantially pure HNS" is a preparation of HNS, which has been isolated or synthesized and which is greater than about 90% free of contaminants. Preferably, the material is greater than 80%, 85%, 90%, 91%, 92%, 93%, 94%, 95%, 96%, 97%, 98%, or even greater than 99% free of contaminants. The degree of purity may be assessed by means known in the art.

The terms "treat" and "treating" as used herein refer to reversing or blocking the progression of the disease in the subject.

As used herein and in the appended claims, the singular forms "a," "an," and "the" include plural referents unless the context clearly dictates otherwise. Thus, for example, reference to "a domain" includes a plurality of such domains and reference to "the protein" includes reference to one or more proteins, and so forth.

Because HNS is a naturally occurring enzyme, it is typically prepared by isolation from a cell culture supernatant medium obtained from a host cell suitable for making the protein. In certain embodiments the host cell is genetically engineered to produce HNS. For example, the genes responsible for the cellular machinery that produce HNS can be placed into a microorganism such as bacteria or fungi. In other embodiments, the genes responsible for the cellular machinery that produce HNS can be placed into a mammalian cell. Non-limiting examples of mammalian cells that may be used include BALB/c mouse myeloma line (NSO/1, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); human fibrosarcoma cell line (HT1080); baby hamster kidney cells (BHK, ATCC CCL 10); Chinese hamster ovary cells+/−DHFR(CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2).

In certain aspects provided herein, the culture conditions for the host cells are optimized to produce a high level of HNS with minimal levels of contaminants. In another aspect provided herein, the process of purifying HNS is intended for use with biological materials, particularly crude mixtures containing HNS and other contaminating proteins, referred to as starting material samples or bulk material. In accordance with one aspect provided herein, a method for the purification of HNS is described, in particular for the purification of recombinant human HNS (rhHNS), from a crude preparation of the culture medium of the recombinant process or bulk material. The rhHNS obtained by this method has a high degree of purity and high specific bioactivity (e.g., in the range of at least 10 units/mg, at least 15 units/mg, at least 20 units/mg, at least 25 units/mg, at least 30 units/mg, at least 35 units/mg, at least 40 units/mg, at least 45 units/mg, at least 47 units/mg, at least 50 units/mg, at least 60 units/mg, at least 70 units/mg, at least 75 units/mg, at least 85 units/mg, at least 90 units/mg, at least 100 units/mg, or more), and is practically free from host cell proteins which are present in the culture medium and from nucleic acids or other contaminants contained in the host cells used in the recombinant process.

In one embodiment, the sample of HNS is initially constituted by collecting cell culture supernatant medium. It is contemplated that the crude solution may be filtered or concentrated and subjected to one or more steps to remove contaminants derived from the cell culture to yield bulk material. The purification process as described herein may include one or more subsequent chromatography steps (e.g., at least one, at least two, at least three, at least four, at least five, at least six, at least seven, at least eight, at least nine, at least ten, or more chromatography steps) in order to achieve a desired degree of purity of HNS.

In certain embodiments the semi-purified material is first captured by exposure to mercapto-ethyl-pyridine. In one embodiment the mercapto-ethyl-pyridine is 4-mercapto-ethyl-pyridine linked to a cellulose matrix.

In another embodiment, the HNS material is subjected to viral inactivation prior to being further purified. Viral inactivation may be accomplished, for example by adding 1% Tween 80 and 0.3% TnBP to in-process HNS samples or media and holding at ambient temperature for 3-16 hours. This step may be performed at early point in the purification scheme. TnBP then must be removed from the product during the polishing steps. Further, filtration of the HNS composition using a 0.2 μm filter may be incorporated into any loading step.

In yet other embodiments, the resulting HNS material is optionally reduced in volume prior to column chromatography purification. In other embodiments, the volume is reduced following recovery of the enriched HNS eluate following the column chromatography steps.

In certain embodiments, methods and processes for purifying HNS by a sequence of chromatography steps are included. In certain embodiments, the performance of each of the disclosed column chromatography purification steps need not necessarily be performed. Similarly, to the extent the multiple column chromatography steps are disclosed, such steps need not be performed sequentially or in the recited order. For example, in certain embodiments, the HNS is purified using at least one, at least two, at least three, at least four or more column chromatography purification steps. Similarly, in certain embodiments one or more of the recited column chromatography steps may be performed multiple times. In some embodiments, one or more of the chromatography steps includes loading, equilibrating, washing, and eluting of the chromatography medium or resin. Notwithstanding the foregoing statements regarding the sequential performance of each of the chromatography purification steps, it should be understood that the individual components which comprise each of the column chromatography purification steps are intended be performed in the order recited. For example, as will be appreciated by one of skill in the art, the steps of loading, equilibrating, washing, and eluting which generally comprise each chromatography purification step are intended to be performed in the recited order.

Exemplary purification techniques include batch chromatography and column chromatography. In some embodiments a HNS composition is contacted with a series of chromatographic media during purification. In certain embodiments, the chromatography media or resins include one or more anionic exchange resin. In another embodiment, the chromatography media or resin includes one or more hydrophobic interaction resin. In yet another embodiment, the chromatography media or resin includes one or more hydroxyapatite resin. In other embodiments, the chromatography media or resin includes one or more cationic exchange resin.

In certain embodiments, the chromatography media or resins include an anionic exchange resin, a hydrophobic interaction resin, a hydroxyapatite resin, and a cationic exchange resin. In certain embodiments, the extracted material is purified using a column packed with Q Sepharose, followed by a column packed with Phenyl Sepharose, followed by a column packed with ceramic hydroxyapatite Type I; and finally followed by another column packed with SP Sepharose. The contemplated steps for purifying the extracted material need not all be performed. For example, in certain embodiments the extracted material is purified using a column packed with Q Sepharose, followed by a column packed with Phenyl Sepharose, followed by a column packed with ceramic hydroxyapatite Type I. Similarly, the contemplated steps for purifying the extracted material need not all be performed in any particular order. For example, in certain embodiments, the extracted material is purified using a column packed with Q Sepharose, followed by a column packed with Phenyl Sepharose, followed by another column packed with SP Sepharose; finally followed by a column packed with ceramic hydroxyapatite Type I. In each of the forgoing embodiments, each of the columns is optionally washed with buffered or other aqueous solution followed by elution of HNS using an aqueous solution. In certain embodiments, the HNS composition is eluted from the chromatography medium between each step. It is contemplated that each elution step may be repeated one or more times before advancing to the next purification step. In certain embodiments the extracted material is further purified by filtration. In yet other embodiments, the extracted material is subjected to viral inactivation before or after chromatography; virus removal can be also achieved during chromatography step.

In one embodiment, the chromatography media or resins comprise an anionic exchange resin. In certain embodiments, contacting the HNS composition with the anionic exchange chromatography resin is, for example, the first, second, third or fourth chromatographic step. Various chromatographic resin or medium may be employed, including, for example, resins from GE HealthCare, Tosoh Biosciences, Applied Biosystems, Bio-Rad, and Pall. Examples of suitable anionic exchange chromatography media are diethylaminoethyl (DEAE), quaternary aminoethyl (QAE) or quaternary ammonium (O) resin. In certain embodiments, the anionic exchange chromatography resin is a Q sepharose fast flow resin.

In another embodiment, the process of purification of HNS comprises a hydrophobic interaction chromatography (HIC) step. In some embodiments, the HNS composition is contacted with a hydrophobic interaction chromatography resin as an intermediate step in the purification process. In other embodiments, contacting the HNS composition with the hydrophobic interaction chromatography resin is, for example, the first, second, third or fourth chromatographic step. Examples of suitable hydrophobic interaction chromatography media include phenyl, octyl, butyl, hexyl, propyl, PPG, or ether. In certain embodiments, purification of the HNS extract is performed using a Phenyl Sepharose 6 Fast Flow column. In certain embodiments, the HNS composition or eluate resulting from contact with the hydrophobic interaction chromatography resin is further contacted with a hydroxyapatite chromatography resin.

In yet another embodiment, the chromatography media or resin comprises a hydroxyapatite (HA) resin. In other embodiments, contacting the HNS composition with the hydroxyapatite resin is, for example, the first, second, third or fourth chromatographic step. In some embodiments, the extract containing HNS is purified using a column packed with ceramic hydroxyapatite Type I. In some embodiments, the extract containing HNS is purified using a column packed with ceramic hydroxyapatite Type II. In yet another embodiment the HNS composition or eluate collected from the interaction with the hydroxyapatite chromatography resin is further contacted with a cationic exchange chromatography resin.

In certain embodiments, the HNS composition is further purified using a cationic exchange chromatography step. In certain embodiments, the purification using a cationic exchange chromatography step is an intermediate step in the purification of HNS. In other embodiments, contacting the HNS composition with the cationic exchange chromatography resin is the first, second, third, fourth or last chromatographic step. In some embodiments, the chromatography media or resin comprises a cationic exchange resin. Examples of suitable cationic exchange chromatography media include chromatography media such as carboxymethyl (CM), sulfopropyl (SP) or methyl sulfonate (S). In some embodiments, the cationic exchange chromatography resin is a SP sepharose fast flow resin.

In one embodiment the HNS obtained following the cationic exchange step is further filtered. In certain embodiments, the HNS is further filtered by, for example, diafiltration or ultrafiltration.

In one step, the purification occurs when the material containing the crude HNS is loaded onto a matrix and pre-equilibrated. The matrix is then washed to remove impurities. It is contemplated that column characteristics may be altered in bore size and length to allow elution with various gradients. As will be appreciated by one of skill in this art, the washing and elution solvents are determined by the matrix used and the polarity of the HNS in such an environment.

Extraction and/or purification of HNS from the bulk HNS composition from an anionic exchange chromatography resin can be optimized upon adjustment of pH levels. For example, a pH level of 7.0 has been shown to optimize extraction and purification. Accordingly, in certain embodiments, the pH of the unpurified bulk FINS composition is adjusted to a pH of about 7.0 prior to contacting the HNS with the anionic exchange chromatography resin. In certain embodiments, the material to be loaded on the anion exchange column is adjusted from about 50 mM to about 100 mM NaAcetate. In some embodiments, the solution containing the HNS composition to be loaded on the anionic exchange resin has a sodium acetate concentration from about 50 to about 100 mM. It has been determined that a conductivity of from about 3-4 mS/cm of the HNS composition facilitates the removal of high pI HNS species using anionic exchange chromatograph resins. Accordingly, in certain embodiments, the conductivity of the HNS composition is adjusted to obtain a conductivity of from about 3 to about 4 mS/cm prior to contacting the HNS composition with anionic exchange chromatography resin. In another embodiment, the conductivity is adjusted to about 3.5 mS/cm prior to contacting the HNS composition with the anionic exchange chromatography resin. In certain embodiments, the HNS composition is viral inactivated prior to loading on the anionic exchange column. In yet another embodiment, the HNS composition is filtered using a 0.2 µm filter prior to loading on the anionic exchange column.

In one embodiment, the anionic exchange column is washed with about 5 column volumes of a buffer containing about 20 mM MES-Tris and about 20 mM NaCl at a pH of about 7.0 prior to elution of the enriched HNS composition from the anion exchange column. In certain embodiments there are additional elution steps between contacts with each chromatography resin. In one embodiment, the HNS is eluted from the anionic exchange chromatography resin using a buffer constituting about 20 mM MES-Tris and about 180 mM NaCl at about pH 7.0. In certain embodiments, the percent recovery of the enriched HNS in the flow through and wash is measured by absorbance units, enzyme activity or ELISA. In one embodiment, the host cell protein clearance is about two fold after this step. In another embodiment, the process removes from about 10 to about 25% of a high pI HNS. In yet another embodiment, the removal of the high pI HNS leads to improved solubility.

In certain embodiments, the hydrophobic interaction resin is equilibrated with a buffer comprising about 20 mM MES-Tris and a NaCl concentration of about 1.1 to 1.5 M, at a pH of about 7.0 and a conductivity of from about 90 to about 120 mS/cm prior to contacting the HNS composition with the hydrophobic interaction column. Such concentrations, pH and conductivity facilitate the binding of HNS to the hydrophobic interaction column, thereby optimizing the purification of the HNS composition.

In certain embodiments, the eluate from the anionic exchange chromatography step containing enriched HNS is the starting material for the hydrophobic interaction step. In one embodiment, the NaCl concentration of the HNS composition is adjusted to achieve a NaCl concentration of from about 1.1 M to about 1.5 M NaCl prior to contacting the HNS composition with the hydrophobic interaction column. In another embodiment, the NaCl concentration is adjusted to about 1.2 M prior to contacting the HNS composition with the hydrophobic interaction column. The pH of the HNS composition is adjusted to about 7.0 prior to being contacted with the hydrophobic interaction column. In some embodiments, the HNS composition is adjusted to obtain a conductivity of from about 85 to 120 mS/cm at 25° C. prior to contacting the HNS composition with the hydrophobic interaction column. In some embodiments, the HNS composition is adjusted to obtain a conductivity of from about 90 to 110 mS/cm at 25° C. prior to contacting the HNS composition with the hydrophobic interaction column.

In certain embodiments, the HNS composition adsorbed to the hydrophobic interaction resin is washed with 4 column volumes of a buffer comprising about 20 mM MES-Tris to wash out impurities and a NaCl concentration of from about 1.1M to about 1.5M, at a pH of about 7.0. In yet another embodiment, the NaCl concentration is about 1.2M.

In one embodiment, the hydrophobic interaction column is eluted with about 4 column volumes of a buffer containing about 20 mM MES-Tris and about 180 to 220 mM NaCl at a pH of about 7.0 to elute the enriched HNS composition from the hydrophobic interaction column. In certain embodiments there are additional elution steps.

In one embodiment, the HNS is eluted from the hydrophobic interaction chromatography resin using a buffer constituting about 20 mM MES-Tris and about 200 mM NaCl at about pH 7.0 with a conductivity range from about 19 to about 23 mS/cm at 25° C. to optimize the recovery of purified HNS. In another embodiment, the pH range is from about 6.9 to 7.1. In certain embodiments, the percent recovery of the enriched HNS in the flow through and wash is measured by absorbance units, enzyme activity or ELISA. In one embodiment, the host cell protein clearance is about 35 to 45 fold after this step.

In certain embodiments, pooled eluates of enriched HNS obtained from the hydrophobic interaction column may be used as the starting material for purification employing a hydroxyapatite column. In some embodiments, the solution containing the HNS composition after elution from the hydrophobic interaction column is adjusted to a concentration of about 2 mM to about 4 mM of NaPO4 to optimize purification. In certain embodiments, the concentration of NaPO4 is adjusted to about 2 mM and a pH of about 7.0+0.1. In one embodiment, the equilibration buffer contains about 20 mM MES-Tris and about 200 mM NaCl at about pH 7.0. In certain embodiments, the pH of the equilibration buffer is adjusted to from about 7.0 to about 7.2. In yet another embodiment, the HNS composition is filtered using a 0.2 µm filter prior to loading on the anionic exchange column. In another embodiment, the equilibration buffer contains about 2 mM NaPO4, about 20 mM MES-Tris and about 200 mM NaCl at a pH of about 7.0.

In one embodiment, the hydroxyapatite column is washed with about 4 column volumes of a buffer containing about 2 mM to about 4 mM of NaPO4, about 20 mM MES-Tris and about 200 mM NaCl at a pH of from about 7.0 to about 7.2 prior to elution of the enriched HNS composition from the hydroxyapatite column. In another embodiment, the wash buffer contains about 2 mM NaPO4, about 20 mM MES-Tris and about 200 mM NaCl at a pH of about 7.0.

In some embodiments, the HNS contacted with the hydroxyapatite column is eluted with a solution containing about 25 mM NaPO4 at a pH of about 7.4 to about 7.6. In another embodiment, the HNS loaded onto the hydroxyapatite column is eluted with an eluent containing from about 20 mM NaPO4 to about 30 mM NaPO4 at a pH of about 7.0 to about 7.6. In one embodiment, the elution buffer contains about 20 mM NaPO4, about 25 mM MES-Tris at a pH of about 7.5+0.1. In certain embodiments, the elution step may be repeated at least once. In certain embodiments, the percent recovery of the enriched HNS in the flow through and wash is measured by absorbance units, enzyme activity or ELISA.

In certain embodiments, pooled eluates of enriched HNS obtained from the hydroxyapatite column may be used as the starting material for purification employing a cationic exchange column. In yet another embodiment, the HNS composition in the starting material is adjusted to obtain a conductivity of about 3 to about 4 mS/cm prior to loading on the cationic exchange column to optimize binding of HNS to the cationic resin. In some embodiments, the conductivity is adjusted to about 3 mS/cm and the solution comprises about 20 mM sodium acetate at about pH 5.0 to optimize binding of HNS to the cationic column. In yet another embodiment, the conductivity of the HNS composition loaded on the cationic exchange resin is about 4 mS/cm and the solution contains about 40 mM sodium acetate at about pH 5.0 to optimize binding of HNS to the cationic column. In another embodiment, the conductivity of the HNS composition loaded on the cationic exchange resin is about 3.5 mS/cm+ 0.5 and the pH is about 5.0. In another embodiment, the HNS composition is filtered using a 0.2 μm filter prior to loading on the cationic exchange column.

In one embodiment, the equilibration buffer contains about 50 mM NaAcetate, from about 20 to about 40 mM NaCl and a pH of about 5.0. In certain embodiments, the pH of the equilibration buffer is adjusted to from about 4.9 to about 5.1. In another embodiment, the equilibration buffer contains about 50 mM NaAcetate, about 20 mM NaCl, a pH of about 5.0, and a conductivity range from about 5 to about 7 mS/cm.

In one embodiment, the cationic exchange column is washed with about 4 column volumes of a buffer containing about 50 mM NaAcetate, from about 20 mM to 40 mM NaCl at a pH of from about 5.0 to about 7.2 prior to elution of the enriched HNS composition from the cationic exchange column. In another embodiment, the wash buffer contains about 50 mM NaAcetate, about 20 mM NaCl, a pH of about 5.0, and a conductivity range from about 5 to about 7 mS/cm.

In some embodiments, the elution of the HNS from the cationic exchange resin is carried out with an eluent comprising about 50 mM sodium acetate and from about 90 mM to about 100 mM NaCl at a pH of about 4.9 to about 5.1. In certain embodiments, the elution of the HNS from the cationic exchange resin is carried out with an eluent comprising about 50 mM sodium acetate and about 90 mM NaCl, at a pH of about 5.0+0.1. In certain embodiments, the eluent has a conductivity range of from about 12 to about 14 mS/cm. In certain embodiments, the elution step may be repeated at least once. In certain embodiments, the percent recovery of the enriched HNS in the flow through and wash is measured by absorbance units, enzyme activity or ELISA.

Another embodiment described herein is a purified HNS which has been isolated by the methods above to a level of purity that is greater than about 90% free of contaminants. Preferably, the material is greater than 80%, 85%, 90%, 91%, 92%, 93%, 94%, 95%, 96%, 97%, 98%, or even greater than 99% free of contaminants. The degree of purity may be assessed by any suitable means known in the art.

Products and processes described herein can be useful for treating and/or preventing any disease/condition in a subject whereby glycosaminoglycans have been found to be important in the development and/or progression of the disease. Certain embodiments can be particularly useful for treating and/or preventing any disease or condition in a subject whereby HNS is either non-functional or absent. Treating a disease also includes exacting a desired improvement in the disease or symptoms of the disease.

The compositions disclosed herein may be used alone or in combination with another therapeutic agent for treating a disease associated with mucopolysaccharoidosis or its sequellae in a subject. These additional therapeutic agents can be administered prior to administration of the composition, or they can be administered at the same time or after administration of the composition. Subjects can be, for example, any human or non-human vertebrate, e.g., dog, cat, horse, cow, pig.

In one embodiment, the formulation buffers for the purified HNS compositions can be a phosphate buffer, such as 5 mM Sodium Phosphate, 145 mM NaCl, pH 7.0. Other suitable buffers are known to the skilled artisan.

In certain embodiments, the final HNS concentration is above 5 grams per liter, above 10 grams per liter, above 15 gram per liter, above 20 grams per liter.

Purified HNS compositions described herein may be administered topically (including ophthalmic and to mucous membranes including vaginal and rectal delivery), pulmonary (e.g., by inhalation or insufflation of powders or aerosols, including by nebulizer; intratracheally, intranasally), orally or parenterally. In certain embodiments parenteral administration is preferred and includes intravenous, intraarterial, subcutaneous, intraperitoneal intramuscular, intracranial, intrathecal or intraventricular, administration.

The embodiments described herein will be further illustrated by the following Examples, which should not be construed as limiting. The articles "a" and "an" as used herein in the specification and in the claims, unless clearly indicated to the contrary, should be understood to include the plural referents. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or the entire group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim dependent on the same base claim (or, as relevant, any other claim) unless otherwise indicated or unless it would be evident to one of ordinary skill in the art that a contradiction or inconsistency would arise. Where elements are presented as lists, (e.g., in Markush group or similar format) it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in so many words herein. It should also be understood that any embodiment or aspect of the invention can be explicitly excluded from the claims, regardless of whether the specific exclusion is recited in the specification. The entire contents of all of the references (including literature references, issued patents and published patent applications and websites) cited throughout this application are hereby expressly incorporated by reference.

EXAMPLES

Hereinafter, the present invention will be described in further detail with reference to examples. It will be obvious to a person having ordinary skill in the art that these examples are illustrative purposes only and are not to be construed to limit the scope of the present invention.

Example 1

All the chromatography steps were performed at the room temperatures. FIG. 11 shows the flow chart of a purification method according to the example 1. Chromatography equipment: Akta Explorer, or Akta Purifier 100, or Akta Pilot by GE Healthcare.

5 M NaCl added to clarified harvest to NaCl concentration 0.5M. pH was adjusted to 7.2-7.6 by adding 1 M Tris.

Column packed with IMAC Sepharose (column volumes 5 ml, 30 or 200 ml, column types HiTrap or XK16 or XK50 from GE Healthcare) was washed by distilled water (2CV), buffer A—20-50 mM Tris-HCl, 0.5 M NaCl, pH 7.4-7.5— (2CV), distilled water (1.5CV), then charged with $Zn^{2+}$ by passing 0.1-0.2 M $ZnCl_2$ (1CV), followed by distilled water (1.5CV) and equilibrated by buffer A (2CV).

Harvest prepared as described above was loaded to equilibrated IMAC column with the flow rate 50-150 cm/h, washed by buffers A (5CV), B—20-50 mM Tris-HCl, 1-2 M NaCl, pH 7.4-7.5 (10CV), C—20-50 mM NaOAc, 100 mM NaCl, 0-10% i-PrOH, pH 6.4 (10CV), D—20-50 mM NaOAc, 20-100 mM NaCl, pH 4.2 (5CV). HNS was eluted with yield >80% by buffer E (20-50 mM NaOAc, 20-100 mM NaCl, 20-100 mM EDTA, pH 4.2) with the flow rate 25-75 cm/h. Started eluate 1 collection when UV signal was 20-50 mAU, stop collect when UV signal drops down to the 5-10% of the peak maximum intensity.

Column was striped by 0.5 M EDTA (3CV), followed by 0.5 M NaOH (5CV) and distilled water (3CV). Stored in 20% EtOH.

FIG. 1 shows the characteristic chromatogram of HNS protein purification by Zn-IMAC chromatography.

FIG. 2 shows a silver staining gel and a western blot gel of Zn-IMAC purification of HNS protein.

Eluate 1 was incubated in low pH for 1-3 hours at the room temperature for virus inactivation. Then, Eluate 1 was diluted by buffer G (20-50 mM NaOAc, pH 4.2) to a conductivity <8 mS/cm.

Column packed with SP Sepharose (GE Healthcare) (volume 5-30 ml, column types HiTrap or XK16 from GE Healthcare) was washed by distilled water (3CV) and equilibrated by buffer F—20-50 mM NaOAc, 1-15 mM EDTA, pH 4.2 (3CV).

Eluate 1 prepared as described above was loaded to equilibrated SP column with the flow rate 5-60 cm/h, washed by buffer F (10 CV), G (5CV) and eluted with yield >80% by buffer H—20-50 mM NaOAc, 150-250 mM NaCl, pH 4.2. Started eluate 2 collection when UV signal was 50 mAU, and stopped when UV signal dropped down to the 5% of the peak maximum intensity.

Striped column by 1 M NaCl (3CV) followed by 0.5 M NaOH (5CV) and distilled water (3CV). Stored in 20% EtOH.

FIG. 3 shows the characteristic chromatogram of HNS protein purification by SP chromatography.

FIG. 4 shows a silver staining gel and a western blot gel of SP purification of HNS protein.

Eluate 2 was diluted by buffer G to conductivity ≤5 mS/cm prior next purification step.

Column packed with Capto MMC (GE Healthcare) (volume 1-10 ml, column types HiTrap or XK16 from GE Healthcare) was washed by distilled water (3CV) and equilibrated by buffer G (3CV).

Eluate 2 prepared as described above was loaded to equilibrated MMC column with the flow rate 100-300 cm/h), washed with by buffer G (10 CV). HNS was eluted with yield >80% by buffer I—20-50 mM NaOAc, 300-400 M NaCl, pH 6.4. Started eluate 3 collection when UV signal was 20 mAU, and stopped when UV signal dropped down to the 5% of the peak maximum intensity.

FIG. 5 shows the characteristic chromatogram of HNS protein purification by Capto MMC chromatography.

FIG. 6 shows a silver staining gel and a western blot gel of Capto MMC purification of HNS protein.

Eluate 3 was diluted by buffer J—20-50 mM Tris-HCl, pH 7.4—to conductivity ≤5 mS/cm prior next purification step.

Column packed with Fractogel TMAE (S) (Merk) (volume 1-10 ml, column types Tricorn 5, or Tricorn 10, or XK16 from GE Healthcare) was washed by distilled water (3CV), 0.1 N HCl (3CV), distilled water (2CV), and equilibrated by buffer J (3CV).

Eluate 3 prepared as described above was loaded to equilibrated column with the flow rate 40-300 cm/h, washed with by buffer J (10 CV). HNS was eluted with yield >80% by buffer K—20-50 mM Tris-HCl, 120-250 mM NaCl, pH 7.4. Started eluate 4 collection when UV signal was 20 mAU, and stopped when UV signal dropped down to the 5% of the peak maximum intensity.

FIG. 7 shows the characteristic chromatogram of HNS protein purification by FRACTOGEL TMAE (S) chromatography.

FIG. 8 shows a silver staining gel and a western blot gel of FRACTOGEL TMAE (S) purification of HNS protein.

Example 2

All the chromatography steps were performed at the room temperatures. FIG. 13 shows the flow chart of a purification method according to the example 2. Chromatography equipment: Akta Explorer, or Akta Purifier 100, or Akta Pilot by GE Healthcare.

5 M NaCl added to clarified harvest to NaCl concentration 0.5M. pH was adjusted to 7.2-7.6 by adding 1 M Tris.

Column packed with IMAC Sepharose (column volumes 5 ml, 30 or 200 ml, column types HiTrap or XK16 or XK50 from GE Healthcare) was washed by distilled water (2CV), buffer A—20-50 mM Tris-HCl, 0.5 M NaCl, pH 7.4-7.5- (2CV), distilled water (1.5CV), then charged with $Zn^{2+}$ by passing 0.1-0.2 M $ZnCl_2$ (1CV), followed by distilled water (1.5CV) and equilibrated by buffer A (2CV).

Harvest prepared as described above was loaded to equilibrated IMAC column with the flow rate 50-150 cm/h, washed by buffers A (5CV), B—20-50 mM Tris-HCl, 1-2 M NaCl, pH 7.4-7.5 (10CV), C—20-50 mM NaOAc, 100 mM NaCl, 0-10% i-PrOH, pH 6.4 (10CV), D—20-50 mM NaOAc, 20-100 mM NaCl, pH 4.2 (5CV). HNS was eluted with yield >80% by buffer E (20-50 mM NaOAc, 20-100 mM NaCl, 20-100 mM EDTA, pH 4.2) with the flow rate 25-75 cm/h. Started eluate icollection when UV signal was 20-50 mAU, stop collect when UV signal drops down to the 5-10% of the peak maximum intensity.

Column was striped by 0.5 M EDTA (3CV), followed by 0.5 M NaOH (5CV) and distilled water (3CV). Stored in 20% EtOH.

FIG. 1 shows the characteristic chromatogram of HNS protein purification by Zn-IMAC chromatography.

FIG. 2 shows a silver staining gel and a western blot gel of Zn-IMAC purification of HNS protein.

Eluate 1 was incubated in low pH for 1-3 hours at the room temperature for virus inactivation. Then, Eluate 1 was diluted by buffer G (20-50 mM NaOAc, pH 4.2) to a conductivity <8 mS/cm.

Column packed with SP Sepharose (GE Healthcare) (volume 5-30 ml, column types HiTrap or XK16 from GE Healthcare) was washed by distilled water (3CV) and equilibrated by buffer F—20-50 mM NaOAc, 1-15 mM EDTA, pH 4.2 (3CV).

Eluate 1 prepared as described above was loaded to equilibrated SP column with the flow rate 5-60 cm/h, washed by buffer F (10 CV), G (5CV) and eluted with yield >80% by buffer H—20-50 mM NaOAc, 150-250 mM NaCl, pH 4.2. Started eluate 2 collection when UV signal was 50 mAU, and stopped when UV signal dropped down to the 5% of the peak maximum intensity.

Striped column by 1 M NaCl (3CV) followed by 0.5 M NaOH (5CV) and distilled water (3CV). Stored in 20% EtOH.

FIG. 3 shows the characteristic chromatogram of HNS protein purification by SP chromatography.

FIG. 4 shows a silver staining gel and a western blot gel of SP purification of HNS protein.

Eluate 2 was pH adjusted to 7,4 by 1 M Tris and diluted by buffer J to conductivity ≤5 mS/cm prior next purification step.

Column packed with DEAE Sepharose (GE Healthcare) (volume 1-10 ml, column types HiTrap, or XK16 from GE Healthcare) was washed by distilled water (3CV), 0.1 N HCl (3CV), distilled water (2CV) and equilibrated by buffer J (3CV).

Eluate 2 prepared as described above was loaded to equilibrated column with the flow rate 40-300 cm/h, washed with by buffer J (10 CV). HNS was eluted with yield >70% by buffer K—20-50 mM Tris-HCl, 120-250 mM NaCl, pH 7.4. Started eluate 3 collection when UV signal was 20 mAU, and stopped when UV signal dropped down to the 5% of the peak maximum intensity.

FIG. 9 shows the characteristic chromatogram of HNS protein purification by DEAE chromatography.

FIG. 10 shows a silver staining gel and a western blot gel of DEAE purification of HNS protein.

Example 3

All the chromatography steps were performed at the room temperatures. FIG. 15 shows the flow chart of a purification method according to the example 3. Chromatography equipment: Akta Explorer, or Akta Purifier 100, or Akta Pilot by GE Healthcare.

5 M NaCl added to clarified harvest to NaCl concentration 0.5M. pH was adjusted to 7.2-7.6 by adding 1 M Tris.

Column packed with IMAC Sepharose (column volumes 5 ml, 30 or 200 ml, column types HiTrap or XK16 or XK50 from GE Healthcare) was washed by distilled water (2CV), buffer A—20-50 mM Tris-HCl, 0.5 M NaCl, pH 7.4-7.5- (2CV), distilled water (1.5CV), then charged with $Zn^{2+}$ by passing 0.1-0.2 M $ZnCl_2$ (1CV), followed by distilled water (1.5CV) and equilibrated by buffer A (2CV).

Harvest prepared as described above was loaded to equilibrated IMAC column with the flow rate 50-150 cm/h, washed by buffers A (5CV), B—20-50 mM Tris-HCl, 1-2 M NaCl, pH 7.4-7.5 (10CV), C—20-50 mM NaOAc, 100 mM NaCl, 0-10% i-PrOH, pH 6.4 (10CV), D—20-50 mM NaOAc, 20-100 mM NaCl, pH 4.2 (5CV), E (20-50 mM NaOAc, 0-25 mM NaCl, 1-25 mM EDTA, pH 4.2). HNS was eluted with yield >80% by buffer L (20-50 mM NaOAc, 150-300 mM NaCl, pH 4.2) with the flow rate 25-75 cm/h. Started eluate 1 collection when UV signal was 20-50 mAU, stop collect when UV signal drops down to the 5-10% of the peak maximum intensity.

Column was striped by 0.5 M EDTA (3CV), followed by 0.5 M NaOH (5CV) and distilled water (3CV). Stored in 20% EtOH.

Eluate 1 was incubated in low pH for 1-3 hours at the room temperature for virus inactivation. Then, Eluate 1 was diluted by buffer G (20-50 mM NaOAc, pH 4.2) to a conductivity <5 mS/cm.

Column packed with Capto MMC (GE Healthcare) (volume 1-10 ml, column types HiTrap or XK16 from GE Healthcare) was washed by distilled water (3CV) and equilibrated by buffer G (3CV).

Eluate 1 prepared as described above was loaded to equilibrated MMC column with the flow rate 100-300 cm/h), washed with by buffer G (10 CV). HNS was eluted with yield >80% by buffer I—20-50 mM NaOAc, 300-400 M NaCl, pH 6.4. Started eluate 2 collection when UV signal was 20 mAU, and stopped when UV signal dropped down to the 5% of the peak maximum intensity.

Eluate 2 was diluted by buffer J—20-50 mM Tris-HCl, pH 7.4—to conductivity ≤5 mS/cm prior next purification step.

Column packed with Fractogel TMAE (S) (Merk) (volume 1-10 ml, column types Tricorn 5, or Tricorn 10, or XK16 from GE Healthcare) was washed by distilled water (3CV), 0.1 N HCl (3CV) and equilibrated by buffer I (3CV).

Eluate 2 prepared as described above was loaded to equilibrated column with the flow rate 40-300 cm/h, washed with by buffer I (10 CV). HNS was eluted with yield >80% by buffer K—20-50 mM Tris-HCl, 120-250 mM NaCl, pH 7.4. Started eluate 3 collection when UV signal was 20 mAU, and stopped when UV signal dropped down to the 5% of the peak maximum intensity.

Example 4

Biological activity was determined by Green Cross Corp. in-house assay. As the reference standard SGSH Protein, CF (R&D systems, Cat. #8380-SU-020) was used.

Measured activity of the purified HNS was found to be 60-150% (n>15) of activity of the standard.

The invention claimed is:

1. A method for purifying a sulfatase comprising the steps of:
   (a) providing a sulfatase-containing solution comprising one or a plurality of impurities, wherein the sulfatase is heparan-N-sulfatase;
   (b) performing a first chromatographic separation of the sulfatase-containing solution using a metal affinity chromatography resin;
   (c) performing a second chromatographic separation using a cation exchange chromatography resin; and
   (d) performing a final chromatographic separation using an anion exchange chromatography resin, wherein the impurities are removed thereby.

2. The method of claim 1, wherein the metal affinity chromatography resin is charged with a divalent metal cation.

3. The method of claim 2, wherein the divalent metal is zinc.

4. The method of claim 1, wherein the cation exchange chromatography resin is selected from the group consisting of a strong cation exchange chromatography resin and a multimodal cation exchange chromatography resin.

5. The method of claim 1, further comprising the step of performing a third chromatographic separation using a cation exchange chromatography resin,
   wherein the resin used in the second chromatographic separation step is a strong cation exchange chromatography resin; and
   wherein the resin used in the third chromatographic separation step is a multimodal cation exchange chromatography resin.

6. The method of claim 1, wherein the anion exchange chromatography resin is selected from the group consisting of a strong anion exchange chromatography resin and a weak anion exchange chromatography resin.

7. The method of claim 1, wherein the sulfatase has a metal ion selected from the group consisting of a calcium ion, a ferrous ion, a ferric ion, and a zinc ion in its active site.

8. The method of claim 1, further comprising a step of low pH virus inactivation.

9. The method of claim 8, wherein the low pH virus inactivation step is performed
   after the first chromatographic separation step and before the second chromatographic separation step; or
   after the second chromatographic separation step and before the final chromatographic separation step.

10. The method of claim 5, further comprising a step of low pH virus inactivation.

11. The method of claim 10, wherein the low pH virus inactivation step is performed
    after the first chromatographic separation step and before the second chromatographic separation step; or
    after the second chromatographic separation step and before the third chromatographic separation step.

12. The method of claim 1, further comprising a step of virus filtration.

13. The method of claim 12, wherein the virus filtration step is performed after the final chromatographic separation step.

14. The method of claim 1, wherein the sulfatase-containing solution is selected from the group consisting of a cell culture harvest and partially purified intermediate solutions.

* * * * *